US010697020B2

(12) United States Patent
Ju et al.

(10) Patent No.: US 10,697,020 B2
(45) Date of Patent: Jun. 30, 2020

(54) MICRORNA-129 AS A BIOMARKER FOR COLORECTAL CANCER

(71) Applicant: THE RESEARCH FOUNDATION FOR THE STATE UNIVERSITY OF NEW YORK, Albany, NY (US)

(72) Inventors: Jingfang Ju, East Setauket, NY (US); Mihriban Karaayvaz, Stony Brook, NY (US); Haiyan Zhai, Holtsville, NY (US)

(73) Assignee: The Research Foundation for The State University of New York, Albany, NY (US)

( * ) Notice: Subject to any disclaimer, the term of this patent is extended or adjusted under 35 U.S.C. 154(b) by 0 days.

(21) Appl. No.: 14/889,212

(22) PCT Filed: May 14, 2014

(86) PCT No.: PCT/US2014/037996
§ 371 (c)(1),
(2) Date: Nov. 5, 2015

(87) PCT Pub. No.: WO2014/186462
PCT Pub. Date: Nov. 20, 2014

(65) Prior Publication Data
US 2016/0090636 A1  Mar. 31, 2016

Related U.S. Application Data

(60) Provisional application No. 61/823,494, filed on May 15, 2013.

(51) Int. Cl.
C12Q 1/68 (2018.01)
A61K 31/7088 (2006.01)
(Continued)

(52) U.S. Cl.
CPC .......... *C12Q 1/6886* (2013.01); *A61K 31/513* (2013.01); *A61K 31/7088* (2013.01);
(Continued)

(58) Field of Classification Search
CPC .............. C12N 2310/141; A61K 48/00; C12Q 1/6886; C12Q 2600/112; C12Q 2600/158; C12Q 2600/178
See application file for complete search history.

(56) References Cited

U.S. PATENT DOCUMENTS

2007/0054287 A1  3/2007  Bloch
2010/0184830 A1  7/2010  Croce et al.

FOREIGN PATENT DOCUMENTS

WO    WO 99/43857 A1    9/1999

OTHER PUBLICATIONS

Bandrés et al. (Molecular Cancer 2006 vol. 5:29, pp. 1-10).*
(Continued)

Primary Examiner — Terra C Gibbs
(74) Attorney, Agent, or Firm — Scully, Scott, Murphy & Presser, P.C.

(57) ABSTRACT

The current disclosure describes methods for identifying subjects that would benefit from treatment with a chemotherapeutic agent. The disclosure is based in part on the observation that miR-129 expression levels are reduced in colorectal cancer. Accordingly, the current disclosure provides therapeutic compositions and methods for altering the expression of a miR-129 effector. Described herein are methods for characterizing the stage of colorectal cancer in a subject, based on the levels of miR-129 expression. The disclosure also identifies miR-129 as a predictive biomarker for cancer diagnosis and the subsequent treatment with directed therapeutic agents including but not limited to miR-129 nucleic acid molecules and/or a chemotherapeutic
(Continued)

agent. The current disclosure also identifies novel therapeutic agents that modulate the level of BCL2, TS and/or E2F3 expression, as well as sensitize a subject to treatment with a chemotherapeutic agent.

7 Claims, 13 Drawing Sheets

Specification includes a Sequence Listing.

(51) Int. Cl.
    *A61P 35/00*     (2006.01)
    *C12Q 1/6886*     (2018.01)
    *A61K 31/7105*     (2006.01)
    *A61K 31/513*     (2006.01)
    *G01N 33/487*     (2006.01)

(52) U.S. Cl.
    CPC ....... *A61K 31/7105* (2013.01); *G01N 33/487* (2013.01); *C12Q 2600/106* (2013.01); *C12Q 2600/112* (2013.01); *C12Q 2600/158* (2013.01); *C12Q 2600/178* (2013.01)

(56) References Cited

OTHER PUBLICATIONS

Matsuoka et al. (Int. J. of Oncology, 2004 vol. 24:217-222).*
Shirasaki et al. (BMC Cancer, 2008 vol. 8:348, pp. 1-12).*
Kaur et al. (Mol. Cancer Ther., 2009 vol. 8:2366-2374).*
Kort et al. (Cancer Res May 1, 2007 (67) (9 Supplement), Abstract 2107).*
Akao et al. (Cancer Letters, 2011 vol. 300:197-204).*
Tyagi et al. (Molecular Cancer Therapeutics, 2002 vol. 1:525-532).*
Liu et al. (PLOS, 2012 vol. 7, No. 4:pp. 1-8).*
Singh et al. (Cancer Letters (2013) vol. 334:211-220). Epub Oct. 13, 2012.*
Wang et al. (FEBS Letters (2013) vol. 587:1779-1786). Epub May 6, 2013.*
Ambros V., "The Functions of Animal microRNAs", Nature 431:350-355 (Sep. 16, 2004).
Bartel D.P., "MicroRNAs: Target Recognition and Regulatory Functions", Cell 136:215-233(Jan. 23, 2009).
Crreras C.W. et al., "The Catalytic Mechanism and Structures of Thymidylate Synthase", Annu. Rev. Biochem. 64:721-762 (1995).
Chen C. et al., "Real-Time Quantification of MicroRNAs by Stem-Loop RT-PCR", Nucleic Acids Research 33(20): e179 (2005).
Croce C.M., "Causes and Consequences of microRNA Dysregulation in Cancer", Nature Reviews—Genetics 10:704-714 (Oct. 2009).
Gottesman M.M. et al., "Multidrug Resistance in Cancer: Role of ATP-Dependent Transporters", Nature Reviews-Cancer 2:48-58 (Jan. 2002).
Hegde S.R. et al., "Systemic and Targeted Therapy by Advanced Colon Cancer", Expert Review of Gastroenterology & Hepatology (Feb. 2008).
Krishan A., "Rapid Flow Cytofluorometric Analysis of Mammalian Cell Cycle by Propidium Iodide Staining", The Journal of Cell Biology 66:188-193 (1975).
Trang P. et al. et al., "Regression of Murine Lung Tumors by the Let-7 MicroRNA", Oncogene 29:1580-1587 (2010).
International Search Report dated Sep. 4, 2014 issued in PCT/US2014/037996.
Nugent, M. et al., "MicroRNAs in colorectal cancer: Function, dysregulation and potential as novel biomarkers", The Journal of Cancer Surgery (2011), vol. 37, pp. 649-654.
Allen, Kristi E. et al., "Resistance May Not Be Futile: microRNA Biomarkers for Chemoresistance and Potential Therapeutics", Molecular Cancer Therapeutics (Oct. 12, 2010), vol. 9, No. 12, pp. 3126-3136.
Li, Su-Chen et al., "Global microRNA profiling of well-differentiated small intestinal neuroendocrine tumors", Modern Pathology (2013), p. 1-12.
Slattery, Martha L. et al., "MicroRNAs and Colon and Rectal Cancer: Differential Expression by Tumor Location and Subtype", Genes Chromosomes Cancer (Mar. 2011), vol. 50, No. 3, pp. 196-206.
Yu, Xing et al., "Gastric juice miR-129 as a potential biomarker for screening gastric cancer", Med Oncol (2013), 30:365.
Bandres, Eva et al., "Epigenetic regulation of microRNA expression in colorectal cancer", Int. J. Cancer (2009), vol. 125, pp. 2737-2743.
Wu, Junjie et al., "miR-129 regulates cell proliferation by downregulating Cdk6 expression", Cell Cycle (May 1, 2010), 9:9, pp. 1809-1818.

* cited by examiner d a b

MICRORNA-129 AS A BIOMARKER FOR COLORECTAL CANCER

CROSS REFERENCE TO RELATED APPLICATIONS

This application claims priority from U.S. Provisional Application No. 61/823,494, filed May 15, 2013, the entire contents of which are incorporated herein by reference.

INCORPORATION BY REFERENCE OF SEQUENCE LISTING

The Sequence Listing in an ASCII text file, named as R8487_US SequenceListing.txt of 2 KB, created on Nov. 28, 2017, and submitted to the United States Patent and Trademark Office via EFS-Web, is incorporated herein by reference.

STATEMENT REGARDING FEDERALLY SPONSORED RESEARCH

This invention was made with government support under CA155019 and CA147966 awarded by the National Institutes of Health. The government has certain rights in the invention.

FIELD OF THE DISCLOSURE

The present disclosure provides methods pertaining to the identification of genes and gene regulators that modulate certain biological pathways in a subject. The current disclosure further provides methods of identifying cancer exhibiting aberrant expression of microRNAs (miRNAs or miR), for therapeutic, prognostic, and diagnostic applications. Namely, methods and compositions related to determining the presence of miRNA-129 in a subject with cancer and determining an appropriate treatment therefore.

BACKGROUND

MicroRNAs (miRNAs, miRs) are a class of highly conserved, non-coding small RNA molecules that mediate translation in a cell or organism by negatively regulating the expression of their target genes and thus causing translational arrest, mRNA cleavage or a combination thereof. See Bartel D P. *Cell*. (2009) 136(2):215-33. By targeting multiple transcripts, miRNAs regulate a wide range of biological processes, including apoptosis, differentiation and cell proliferation, thus aberrant microRNA function can lead to cancer (see Ambros V. *Nature*. (2004) 431(7006):350-5) and as such, miRNAs have recently been identified as biomarkers, oncogenes or tumor suppressors. See, e.g., Croce, C M, *Nat Rev Genet*. (2009) 10:704-714).

Colorectal cancer (CRC) is the third most common malignancy and the second most common cancer-related cause of death in the United States. See, Hegde S R, et al., *Expert review of gastroenterology & hepatology*. (2008) 2(1):135-49). There are many chemotherapeutic agents used to treat cancer; however pyrimidine antagonists, such as fluoropyrimidine-based chemotherapeutic agents (e.g., 5-fluorouracil, S-1) are the gold standard for treating colorectal cancer. Pyrimidine antagonists, block the synthesis of pyrimidine containing nucleotides (Cytosine and Thymine in DNA; Cytosine and Uracil in RNA). Because pyrimidine antagonists have similar structures when compared to endogenous nucleotides, they compete with the natural pyrimidines to inhibit crucial enzymatic activity involved in the replication process leading to the prevention of DNA and/or RNA synthesis and inhibition of cell division.

5-fluoro-1H-pyrimidine-2,4-dione (5-Fluorouracil, 5-FU) is a well known pyrimidine antagonists and is the focus of many adjuvant chemotherapeutic strategies, such as Carac® cream, Efudex®, Fluoroplex®, and Adrucil®. It is well established that 5-FU targets a critical enzyme, thymidylate synthase (TYMS or TS), which catalyzes the methylation of deoxyuridine monophosphate (dUMP) to deoxythymidine monophosphate (dTMP) an essential step in DNA biosynthesis. See, Danenberg P V. *Biochimica et biophysica acta*. (1977) 473(2):73-92. However, despite the steady improvement of 5-FU-based therapy, the patient response rate to 5-FU-based chemotherapy remains modest, due to the development of drug resistance. See, Longley D B, et al., *Apoptosis, Cell Signaling, and Human Diseases*. (2007) p. 263-78.

One major mechanism utilized by tumor cells is to circumvent the apoptotic pathways by developing resistance to common therapeutic agents such as 5-FU. See, Gottesman M M, et al. *Nature Rev. Cancer*. (2002) 2(1):48-58). Thus, it is essential to better understand the mechanisms of drug resistance and to discover novel strategies to further improve the effectiveness of 5-FU.

SUMMARY OF THE DISCLOSURE

The current disclosure reveals that miR-129 is a predictive biomarker for diagnosing colorectal cancer and determining the grade or stage of colorectal cancer in a subject. As disclosed herein the expression of miR-129 is reduced in subjects with colorectal cancer when compared to that of normal control samples or reference samples. Additionally, miR-129 levels were significantly reduced in subjects with stage 2 colorectal cancer, and the reduction of miR-129 expression increased progressively in stage 3 and stage 4 samples. Therefore, the loss of miR-129 activity is a critical event in colorectal tumorigenesis and can be measured as a diagnostic indicator of colorectal cancer progression.

The present disclosure provides a method of diagnosing colon cancer in a subject based on detecting a reduction in miR-129 expression wherein, a biological sample is obtained from the subject in question. In one embodiment, miR-129 expression measured from the subject in question is compared to a control sample in order to determine whether or not colorectal cancer exists in the subject. Whereby, a reduction in miR-129 expression levels relative to a control sample value indicates that the subject has colorectal cancer. Alternatively, when the level of miR-129 expression is elevated or equal to a control sample value, it can be determined that the subject does not have colorectal cancer.

One aspect of the instant disclosure describes a method for characterizing the stage of colorectal cancer in a subject including detecting or measuring miR-129 in a biological sample, wherein the level of miR-129 expression is reduced when compared to the level exhibited by control samples or data sets obtained from normal noncancerous patients but increased when compared to the level of miR-129 expression exhibited by, for example, stage two colorectal cancer reference samples or data sets thereof indicates that the subject has stage one colorectal cancer.

In one embodiment of the current disclosure, the stage of colorectal cancer is characterized by comparing the level of miR-129 expression in a biological sample to that of two or more reference samples. For example, where the level of miR-129 expression is reduced when compared to the level of miR-129 expression exhibited by a stage one colorectal reference sample or data sets thereof but, the level of miR-129 expression in the test sample is greater than that of a grade three colorectal cancer reference sample or data sets thereof, the subject can be diagnosed with stage two colorectal cancer.

In another embodiment of the current disclosure, the method for characterizing the stage of colorectal cancer in a subject includes a biological sample exhibiting a reduced level of miR-129 expression when compared to the level of miR-129 expression exhibited by a stage two colorectal cancer reference sample or data sets thereof but, the level of miR-129 expression in the test sample is greater than that of a grade four colorectal cancer reference sample or data sets thereof, the subject can be diagnosed with grade three colorectal cancer.

In certain embodiments the survival time of a subject diagnosed with stage three colorectal cancer can be determined based on miR-129 expression levels. For example, a subject having a two to three-fold increase in miR-129 expression over that of a normal subject or control sample is significantly less likely to survive beyond fifty months after diagnosis. Conversely, a subject exhibiting miR-129 expression that is less than two to three fold above that of a normal subject or control sample, has a high likelihood of surviving beyond fifty months post diagnosis. In a specific embodiment, a subject that exhibits reduced miR-129 expression levels when compared to that of a control sample, is diagnosed with colorectal cancer. When such miR-129 expression levels are above 2.5 to 2.8-fold, inclusive, the subject has a low likelihood of surviving beyond 50 months post diagnosis.

In yet another embodiment of the current disclosure, the method for characterizing the stage of colorectal cancer in a subject includes a biological sample exhibiting a reduced level of miR-129 expression when compared to the level of miR-129 expression exhibited by stage three colorectal cancer reference samples or data sets thereof. This indicates that the subject has stage four colorectal cancer.

As demonstrated herein, significant reductions in miR-129 expression levels have been observed in cancer samples relative to non-cancerous control samples or reference samples which have been correlated to the resistance or responsiveness of the cancerous cells to treatment with a chemotherapeutic agent. According to the present methods, miR-129 expression is detected in a biological sample obtained from a subject, wherein a reduced level of miR-129 expression in the sample identifies the subject as resistant to chemotherapy.

In one embodiment, miR-129 expression measured from the subject in question, generally a subject having cancer, is compared to a reference value or control value in order to determine whether or not the subject will likely be responsive to treatment with a chemotherapeutic agent.

The current disclosure describes methods by which the level of miR-129 expression is used to characterize a subject according to their likelihood of responding to treatment with a chemotherapeutic agent, such as a fluoropyrimidine-based chemotherapeutic agent, or an inhibitor of thymidylate synthase expression or activity, or an inhibitor of E2F3 expression or biological activity. This characterization is also a useful means of directing treatment to a subject with colorectal cancer, exhibiting reduced miR-129 expression levels, with a therapeutic agent that increases miR-129 expression levels or activity and thus, sensitizes the subject to treatment with a chemotherapeutic agent.

The current disclosure further demonstrates that the introduction of a miR-129 nucleic acid to tumors enhanced the responsiveness of a tumor to treatment with chemotherapeutic agents. Moreover, the data described herein shows that increasing miR-129 reduced the expression of E2F3, a transcription factor protein that regulates cell cycle progression and reduced the expression of thymidylate synthase protein levels, which resulted in increased cellular proliferation and increased efficacy of chemotherapeutic agents.

In another aspect of the present disclosure, a therapeutically effective amount of miR-129 is provided to colon cancer stem cells to reduce the size of the tumor and thus progression of the cancer. In certain embodiments, miR-129 is delivered to a subject diagnosed with miR-129 (i.e., having a reduced level of miR-129 expression, when compared to a control sample) via lentiviral vector, subcutaneous injection or intravenous injection.

Classification of patients based on miR-129 expression levels not only predicts the patient's responsiveness to chemotherapy, but also permits personalized design of treatment options. For example, for subjects identified as having miR-129 expression levels that are reduced or equal to that of a control sample, chemotherapy is not expected to be effective and should not be administered alone. However, these subjects can be treated with an agent as described herein that sensitizes a subject to chemotherapy. For subjects identified as having miR-129 expression levels that are equal to or elevated relative to control samples the subjects will likely be responsive to chemotherapy and chemotherapy should be administered. In a further embodiment, the chemotherapy used in the prescribed method is a fluoropyrimidine or antifolate compound, including but not limited to 5-FU.

The present disclosure further provides a method of treating cancer in a subject who has been identified as exhibiting a reduced level of miR-129, by administering to the subject an effective amount of an agent that inhibits expression or activity of BCL2, TS, or E2F3 or effectors thereof, wherein inhibition of expression of BCL2 sensitizes the cancer to the chemotherapeutic treatment.

In one embodiment of the current disclosure, the agent that inhibits BCL2 is a nucleic acid, a small molecule, an antibody or a peptide, any of which directly or indirectly inhibits the expression or anti-apoptotic activity of BCL2.

Another embodiment of the current disclosure, the agent that inhibits TS is a nucleic acid, a small molecule, an antibody or a peptide, any of which directly or indirectly inhibits the expression or biological activity of TS.

Another embodiment of the current disclosure, the agent that inhibits E2F3 is a nucleic acid, a small molecule, an antibody or a peptide, any of which directly or indirectly inhibits the expression or biological activity of TS.

Figure 1:
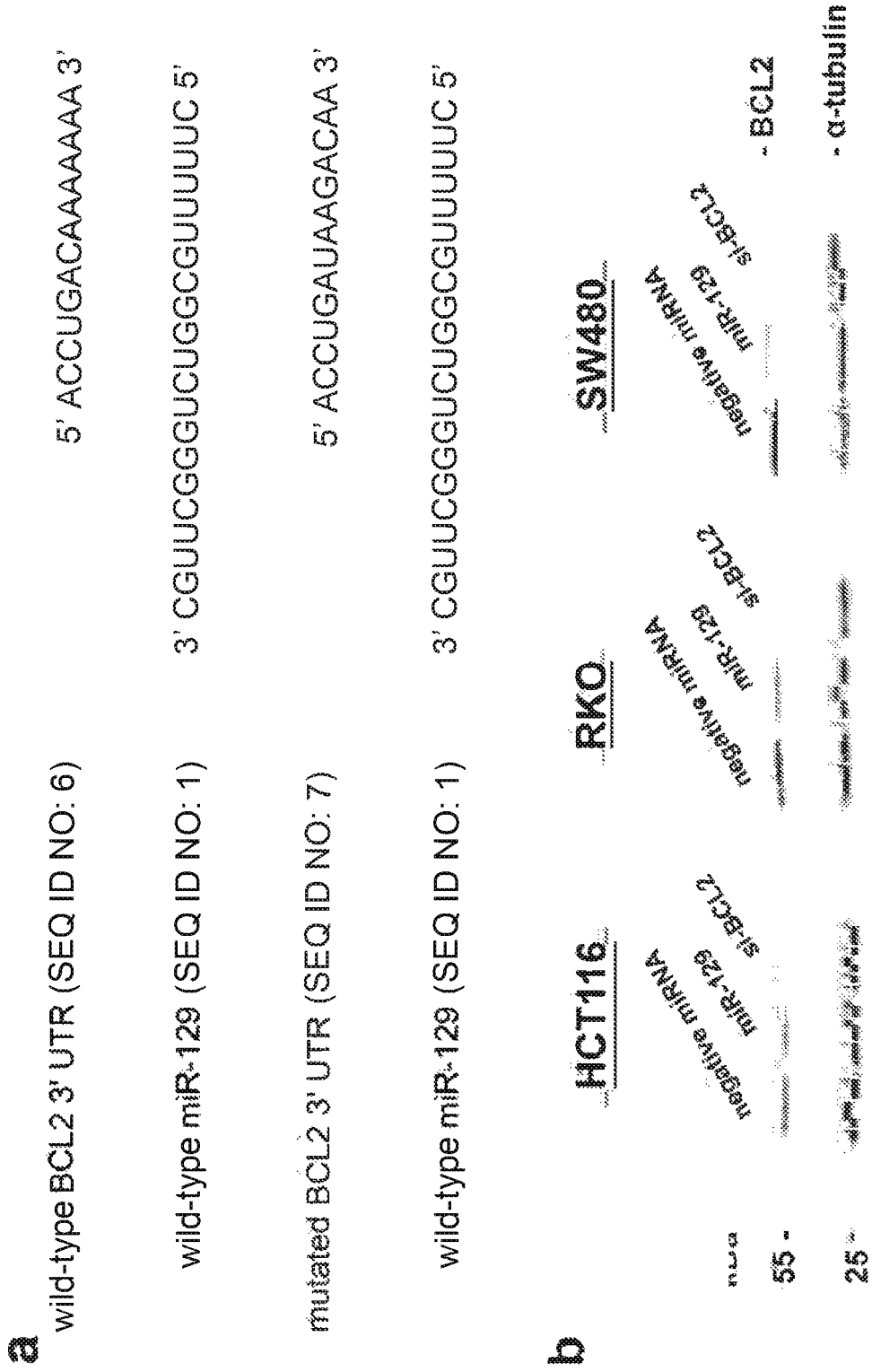
FIG. 1. BCL2 is the direct target of miR-129. (a) A putative miR-129 binding site (CAAAAA) exists in the 3'-UTR of BCL2 mRNA set forth in oligonucleotide sequence ACCUGACAAAAAA (SEQ ID NO: 6) and three point mutations were generated in the binding site as set forth in oligonucleotide sequence ACCUGAUAAGACAA (SEQ ID NO: 7). (b) Ectopic expression of miR-129 or siRNA against BCL2 (siBCL2) in HCT116, RKO and SW480 cells decreased BCL2 protein levels by Western immunoblot analysis. (c) Transfection of miR-129 inhibited firefly luciferase activity of pMIR-REPORT-3'-UTR-BCL2 (wild-type, wt) and such inhibition was absent with mutations in the miR-129 binding site (mutant, mut). The impact of miR-129 on BCL2 expression was normalized and compared to the negative miRNA (n=3, P<0.05).
Figure 1:
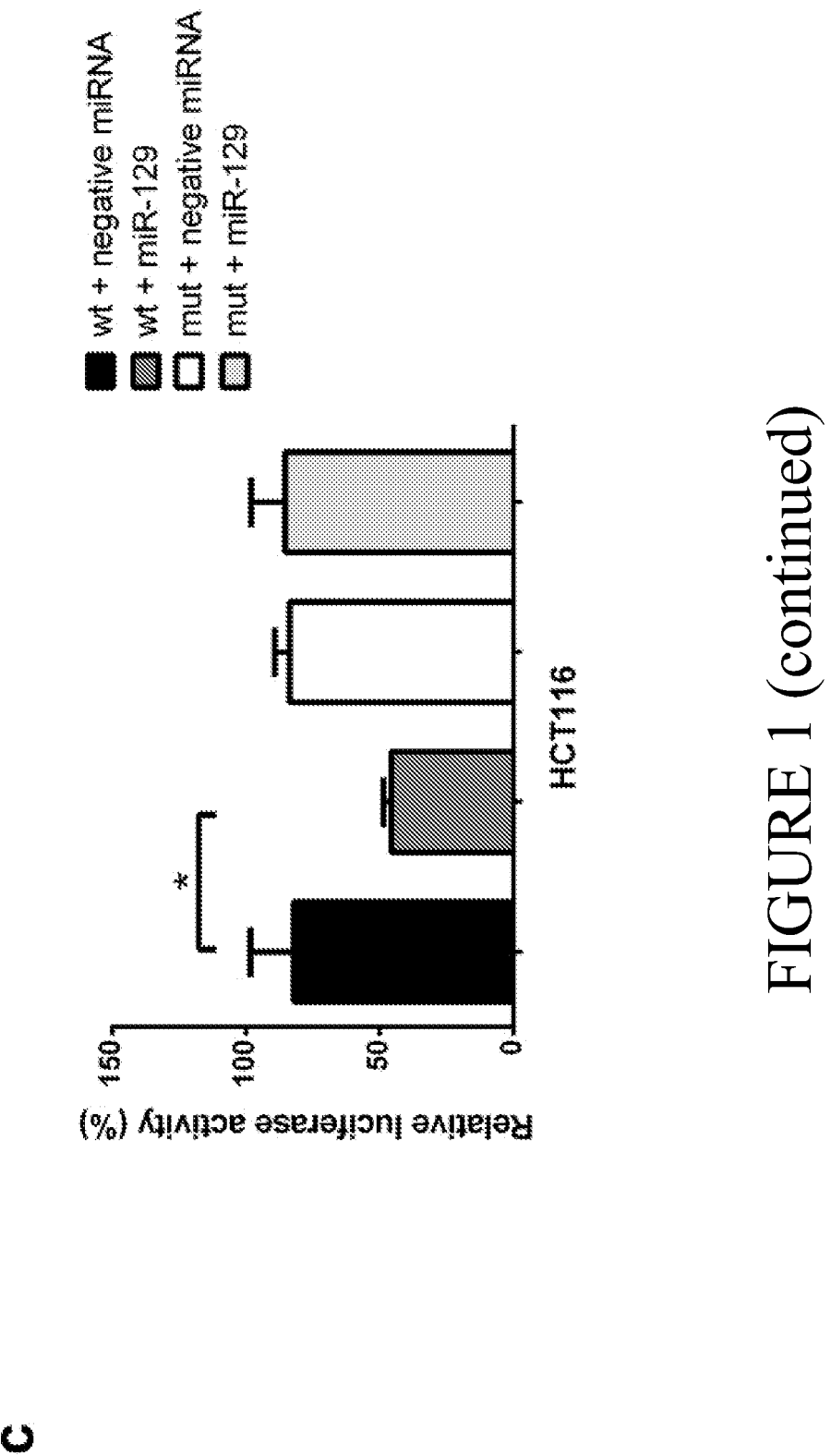

TABLE 1 miR-129 regulated targets. miR-129 apoptosis related targets, acting in the intrinsic apoptosis pathway.

| Gene symbol | Gene title | Fold change (miR-129/neg) |
|---|---|---|
| BCL2 | B-cell CLL/lymphoma 2 | 0.006 |
| BCL2A1 | BCL2-related protein A1 | 0.04 |
| BIRC3 | baculoviral IAP repeat containing 3 | 0.28 |
| PARP2 | poly (ADP-ribose) polymerase 2 | 0.47 |
| APAF1 | apoptotic peptidase activating factor 1 | 2.44 |
| BAX | BCL2-associated X protein | 27.77 |
| CASP2 | caspase 2, apoptosis-related cysteine peptidase | 7.68 |
| CASP3 | caspase 3, apoptosis-related cysteine peptidase | 1.27 |
| CASP7 | caspase 7, apoptosis-related cysteine peptidase | 4.75 |
| CASP9 | caspase 9, apoptosis-related cysteine peptidase | 2.53 |
| MCL1 | myeloid cell leukemia sequence 1 (BCL2-related) | 3.81 |

DETAILED DESCRIPTION OF THE DISCLOSURE

The current disclosure reveals that miR-129 is a predictive biomarker for diagnosing colorectal cancer in a subject and determining the grade or stage of colorectal cancer in a patient. In one aspect of the present disclosure the expression of miR-129 is reduced in biological samples obtained from subjects with colorectal cancer when compared to that of normal control samples, whereby a reduction in miR-129 expression indicates the presence of cancer. More specifically, miR-129 levels were significantly reduced in subjects with stage 2 colorectal cancers, and the reduction of miR-129 expression increased progressively in stage 3 and stage 4 samples. Therefore, the loss of miR-129 activity is a critical event in colorectal tumorigenesis and can be used as a diagnostic indicator of colorectal cancer progression.

Herein, a novel mechanism for cancer prevention and directed treatment is described whereby, miR-129 blocks anti-apoptotic proteins in a cell, which activates the intrinsic apoptosis pathway. Moreover, the data described herein shows that increasing miR-129 expression reduces the expression of E2F3 protein levels, a transcription factor protein that regulates cell cycle progression and reduces the expression or activity of thymidylate synthase protein levels, resulting in increased cellular proliferation and increased efficacy of chemotherapeutic agents.

Therefore, in certain aspects of the current disclosure miR-129 can be used as a therapeutic agent to reduce tumor size and prohibit tumor progression. More specifically, the current disclosure demonstrates that providing nucleic acid molecules of miR-129 to colorectal tumor samples enhanced the responsiveness of the tumor to treatment with chemotherapeutic agents.

Taken together, the level of miR-129 expression can be used to characterize a subject: (i) as having colorectal cancer, (ii) according to their likelihood of survival, (iii) according to their likelihood of responding to treatment with a chemotherapeutic agent, such as a fluoropyrimidine-based chemotherapeutic agent, or an inhibitor of thymidylate synthase, or E2F3. The characterization of miR-129 expression of a subject is also a useful means of directing treatment to a subject with colorectal cancer that exhibits reduced miR-129 expression levels, e.g., providing a therapeutic agent that increases miR-129 expression levels or activity and/or sensitizes the subject to treatment with a chemotherapeutic agent.

Terminology

The term "microRNA" or "miRNA" or "miR" refers to small non-coding ribose nucleic acid (RNA) molecules that are capable of regulating the expression of genes through interacting with messenger RNA molecules (mRNA), DNA or proteins.

"microRNA-129," or "miR-129," or "miRNA-129" as used herein refers a nucleic acid having a sequence of, CUUUUUGCGGUCUGGGCUUGC (SEQ ID NO. 1). MiR-129 is also referred to in the field as, hsa-miR-129 or hsa-miR-129-5p, with Accession number(s) MI0000252 and MIMAT0000242.

The term "increase" or "greater" or "elevated" means at least more than the relative amount of an entity identified (such as, miR-129 expression), measured or analyzed in a control sample. Non-limiting examples include, but are not limited to, a 5-10%, 10-20% increase over that of a control sample, or at least 20%, 30%, 40%, 50%, 60%, 70%, 80%, 90%, 100%, 200% or greater increase over that of a control sample, or at least a 0.25 fold, 0.5 fold, 1 fold, 1.5 fold, 2 fold, 2.1 fold, 2.2 fold, 2.3 fold, 2.4 fold, 2.5 fold, 2.6 fold, 2.7 fold, 2.8 fold, 2.9 fold, 3 fold, 4 fold, 5 fold, 10 fold, 11 fold or greater, increase relative to the entity in the control sample.

The term "decrease" or "reduction" means at least lesser than the relative amount of an entity identified, measured or analyzed in a control sample. Non-limiting examples include, but are not limited to, 5-10%, 10-20% decrease compared to that of a control sample, or at least 20%, 30%, 40%, 50%, 60%, 70%, 80%, 90%, 100%, 200% or greater decrease when compared to that of a control sample, or at least a 0.25 fold, 0.5 fold, 1 fold, 1.5 fold, 2 fold, 2.1 fold, 2.2 fold, 2.3 fold, 2.4 fold, 2.5 fold, 2.6 fold, 2.7 fold, 2.8 fold, 2.9 fold, 3 fold, 4 fold, 5 fold, 10 fold, 11 fold or greater, decrease relative to the entity in the control sample.

The phrase "reducing the level or activity" or "elevate the level or activity" is employed herein to refer to decreasing the level or activity; or increasing the level or activity of an entity (e.g., miR-129) including but not limited to, a gene, peptide or molecule within a cell, respectively. Non-limiting examples of the activity or level of a molecule of the current disclosure includes the amount of microRNA present in a cell, or sample. In a specific embodiment of the current disclosure, the amount of microRNA present is the level of miR-129 present in a cell, sample or subject. Yet another example of the activity or level as utilized in the current disclosure is the ability of miR-129 to bind BCL2, TS or E2F3 in a cell or subject and modulate the activity thereof. In one embodiment, the level or activity includes a reduction in the expression of BCL2 or in the ability of BCL2 to induce apoptosis.

A "reduced level of miR-129 expression" as used in the current disclosure shall mean a decrease in the amount of miR-129 RNA or coding DNA present in a cell, organism or sample. In certain embodiments the reduction in miR-129 expression is obtained by comparing the level of mir-129 expression in a test sample or subject to that of a normal control sample. In a specific embodiment the reduction in the level of miR-129 expression is 5-10%, 10-20% decrease compared to that of a control sample, or at least 20%, 30%, 40%, 50%, 60%, 70%, 80%, 90%, 100%, 200% or greater decrease when compared to that of a control sample, or at least a 0.25 fold, 0.5 fold, 1 fold, 1.5 fold, 2 fold, 2.1 fold, 2.2 fold, 2.3 fold, 2.4 fold, 2.5 fold, 2.6 fold, 2.7 fold, 2.8 fold, 2.9 fold, 3 fold, 4 fold, 5 fold, 10 fold, 11 fold or greater, decrease relative to the amount of miR-129 detected in a control sample.

A "reduced level of BCL2 expression" or "reduced level of thymidylate synthase expression" or "reduced level of E2F3 expression" as used in the current disclosure shall mean a decrease in the amount of BCL2, thymidylate synthase or E2F3 protein, RNA (e.g., mRNA), or coding DNA present in a cell, organism or sample, respectively. In a specific embodiment the reduction in the level of BCL2 expression is 5-10%, 10-20% decrease compared to that of a control sample, or at least 20%, 30%, 40%, 50%, 60%, 70%, 80%, 90%, 100%, 200% or greater decrease when compared to that of a control sample, or at least a 0.25 fold, 0.5 fold, 1 fold, 1.5 fold, 2 fold, 2.1 fold, 2.2 fold, 2.3 fold, 2.4 fold, 2.5 fold, 2.6 fold, 2.7 fold, 2.8 fold, 2.9 fold, 3 fold, 4 fold, 5 fold, 10 fold, 11 fold or greater, decrease relative to the amount of BCL2 detected in a control sample.

The term "sensitize," or the phrase "increase sensitivity or responsiveness to", as used in the current disclosure, refers to the ability of an agent (e.g., miR-129 nucleic acid) treatment disclosed herein to result in an improved effectiveness of the chemotherapeutic agent (e.g., in killing, inducing apoptosis, or preventing the growth of cancerous cells) in the subject. For example, providing a cell or subject with an effective amount of an agent that reduces the level or activity of BCL2, thymidylate synthase or E2F3 sensitizes a cell, previously resistant, to treatment with a chemotherapeutic agent.

The term "resistant" to a chemotherapeutic agent means that the therapeutic agent fails to achieve the intended therapeutic effects (e.g., killing cells, inducing apoptosis, or preventing or inhibiting the growth of cancerous cells) in the subject being treated. For example, as shown herein, cancerous cells having reduced levels of miR-129 expression are resistant to 5-fluorouracil (a chemotherapeutic agent).

The term "responsive" as used in the current disclosure means a desired reaction of a cell, organism or subject to treatment with a therapeutic agent, such as a chemotherapeutic agent or miR-129 nucleic acid.

The term "binding", "to bind", "binds", "bound" or any derivation thereof refers to any stable, rather than transient, chemical bond between two or more molecules, including, but not limited to, covalent bonding, ionic bonding, and hydrogen bonding. Thus, this term also encompasses hybridization between two nucleic acid molecules among other types of chemical bonding between two or more molecules.

The phrase "effector" or "effectors" refers to any small molecule, protein, ligand, or complex thereof that binds to, or interacts with another protein or nucleotide or combination thereof. The result of this interaction may modulate a biological activity including but not limited to, cellular proliferation, cell-cycle regulation, apoptosis, cell signaling, enzymatic activity, or protein-protein interaction.

The phrase "subject in need thereof" as used herein refers to any mammalian subject in need of a treatment, particularly cancer subjects, including cancer subjects exhibiting reduced levels miR-129 expression. The methods of the current disclosure can be practiced on any mammalian subject that has a risk of developing cancer. Particularly, the methods described herein are most useful when practiced on humans. In a specific embodiment, the subject is a human exhibiting reduced miR-129 expression when compared to that of a control sample or subject.

A "biological sample," "sample" or "samples" to be used in the disclosure can be obtained in any manner known to a skilled artisan. Samples can be derived from any part of the subject, including whole blood, tissue, lymph node or a combination thereof. A "control sample" is a sample which does not contain cancerous cells (e.g., a sample from benign tissues), or a sample which does not exhibit elevated miR-129 levels or activity (e.g., samples from benign or non-cancerous tissues). Non-limiting examples of control samples for use in the current methods include, but are not limited to, non-cancerous tissue extracts (e.g., biopsy), surgical margins extracted from the subject, isolated cells known to have normal miR-129 levels (e.g., reference sample or database), obtained from the subject under examination or other healthy individuals. In one embodiment, the control sample of the present disclosure is benign tissue. In another embodiment of the current disclosure, the amount of miR-129 in a sample is compared to either a standard amount of miR-129 present in a normal cell or a non-cancerous cell, or to the amount of miR-129 in a control sample. The comparison can be done by any method known to a skilled artisan.

A "reference sample" as used herein, shall refer to any type of biological sample or representative data set thereof to which, a characteristic of a control sample or biological sample can be compared. In one embodiment of the current disclosure, a reference sample is tissue obtained from a patient known to have stage 1, 2, 3 or 4 colorectal cancer from which miR-129 expression levels can be readily detected or are already known. In yet another embodiment, the reference sample is tissue obtained from a subject known to be cancer free, or of non-cancerous tissue from which miR-129 expression levels can be detected or are already known.

The term "agent" is employed herein to refer to any kind of compound, molecule or ion and any combination thereof. In one embodiment of the disclosure the agent is a small molecule. In another embodiment of the disclosure, the agent is a biological molecule including, but not limited to, a protein or a peptide or a nucleic acid, or an ion. In yet another embodiment, the agent is an antibody or fragment thereof. In a specific embodiment, the agent is a nucleic acid, such as a microRNA or interfering RNA.

The term "interfering RNA" is employed herein to refer to small interfering RNAs (siRNAs), short hairpin RNAs (shRNAs), microRNAs (miRNAs), antisense oligonucleotides, ribozymes, or any RNA-based molecule that interferes with the expression of a protein from its corresponding gene or modulate the activity of the protein.

The term "compound" as used herein refers to a chemical entity or biological product, or combination of chemical entities or biological products, administered to a subject to treat or prevent or control a disease or condition. The chemical entity or biological product is preferably, but not necessarily a low molecular weight compound, but may also be a larger compound, for example, an oligomer of nucleic acids, amino acids, or carbohydrates including without limitation proteins, oligonucleotides, ribozymes, DNAzymes, glycoproteins, siRNAs, lipoproteins, aptamers, and modifications and combinations thereof.

In the context of this disclosure, the term "small molecule" refers to small organic compounds, including but not limited to, heterocycles, peptides, saccharides, steroids, antibodies and the like. The small molecule modulators can have a molecular weight of less than about 1500 Daltons, 1200 Daltons, 1000 Daltons, or 800 Daltons. In some embodiments, a small molecule modulator is less than 500 Daltons. The small molecules can be modified to enhance efficacy, stability, pharmaceutical compatibility, and the like. Candidate modulator compounds from libraries of synthetic or natural compounds can be screened. Synthetic compound libraries are commercially available from a number of companies including Maybridge Chemical Co. (Trevillet, Cornwall, UK), Comgenex (Princeton, N.J.), Brandon Associates (Merrimack, N.H.), Microsource (New Milford, Conn.), and ChemBridge (San Diego, Calif.). Combinatorial libraries are available or can be prepared according to known synthetic techniques. Alternatively, libraries of natural compounds in the form of bacterial, fungal, plant and animal extracts are available from e.g., Pan Laboratories (Bothell, Wash.) or MycoSearch (NC), or are readily producible by methods well known in the art. Additionally, natural and synthetically produced libraries and compounds may be further modified through conventional chemical and biochemical techniques.

The term "peptide" refers to a linear series of amino acid residues linked to one another by peptide bonds between the alpha-amino and carboxy groups of adjacent amino acid residues.

The term "synthetic peptide" is intended to refer to a chemically derived chain of amino acid residues linked together by peptide bonds. The term synthetic peptide is also intended to refer to recombinantly produced peptides in accordance with the present disclosure.

As used herein, "chemotherapy" or the phrase a "chemotherapeutic agent" is an agent useful in the treatment of cancer. Chemotherapeutic agents useful in conjunction with the methods described herein include any agent that modulates thymidylate synthase, either directly or indirectly. Examples of chemotherapeutic agents include: anti-metabolites such as methotrexate and fluoropyrimidine-based pyrimidine antagonist, 5-fluorouracil (5-FU) (Carac® cream, Efudex®, Fluoroplex®, Adrucil®) and S-1; antifolates, including polyglutamatable antifolate compounds; raltitrexed (Tomudex®), GW1843 and pemetrexed (Alimta®) and non-polyglutamatable antifolate compounds; nolatrexed (Thymitaq®), plevitrexed, BGC945; folic acid analogs such as denopterin, methotrexate, pteropterin, trimetrexate; and purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine. In a specific embodiment of the current disclosure the chemotherapeutic agent is a compound capable of inhibit the expression or activity of genes, or gene products involved in signaling pathways implicated in aberrant cell proliferation or apoptosis, such as, for example, BCL2, thymidylate synthase or E2F3; and pharmaceutically acceptable salts, acids or derivatives of any of the above.

Herein, the term "substantially identical" when used in reference to nucleotide or protein sequences, refers to a nucleotide or protein sequence having an identity of at least 60%, 70%, 80%, 90%, 91%, 92%, 93%, 94%, 95%, 96%, 97%, 98%, 99% or greater to a specified nucleotide or protein sequence.

Diagnostic Methods

The current disclosure reveals that the expression of miR-129 is reduced in subjects with colorectal cancer when compared to that of a control sample and that the reduction of miR-129 expression increases with severity of tumor progression in the subject. When compared to a control sample a biological sampled obtained from a subject that exhibits a reduced level of miR-129 expression identifies the subject as having colorectal cancer. Conversely, wherein the level of miR-129 expression exhibited in a biological sample is equal to or greater than the levels exhibited by control samples or data sets thereof, the subject will be identified as a subject not afflicted with colorectal cancer. Therefore, the present disclosure provides a method of diagnosing colon cancer in a subject based on detecting a reduction in miR-129 expression levels.

In one embodiment, a biological sample is obtained from a subject in question. The biological sample that can be used in accordance with the present disclosure may be collected by a variety of means. Non-limiting examples of applicable collection methods include fine needle aspiration, surgical excision, endoscopic biopsy, excisional biopsy, incisional biopsy, fine needle biopsy, punch biopsy, shave biopsy and skin biopsy. In other embodiments, miR-129 expression levels can be detected from cancer or tumor samples from other body fluids such as whole blood (or the plasma or serum fractions thereof), spinal fluid or lymphatic tissue. In some embodiments, the sample obtained from a subject is used directly without any preliminary treatments or processing, such as fractionation or extraction of DNA or RNA. In certain specific embodiments, a tumor or tumor biopsy is obtained from a subject and fluid from the tumor is removed, e.g., by centrifugation, and the tumor fluid is used as the sample for measuring miR-129 expression levels. In another specific embodiment, the sample is collected from a subject and embedded in paraffin prior to analysis.

After a suitable biological sample is obtained, the level of miR-129 expression in the sample can be determined using various techniques. Generally, the level of miR-129 expression can be determined by any suitable method known to one of skill in the art. In certain embodiments of the current disclosure miR-129 expression levels may be measured by a process selected from q-RT-PCR, Northern blotting, microarray analysis, or RT-PCR. In one embodiment, real-time reverse transcriptase PCR is conducted on a sample, wherein a stem-loop primer is hybridized to the microRNA molecule to be detected, then reverse transcribed with reverse transcriptase enzymes, and then quantified using real-time PCR (See, e.g., Chen, C., et al. *Nucleic Acids Res.* (2005). 33(20): e179). Non-limiting examples of primers applicable to the current methods are referenced in Example 7, below. Additional methods of isolating nucleic acid are well known in the art. See, e.g., US Patent Publication No. 2007/0054287.

A non-limiting example of RNA detection includes the use of miRNA arrays, which are ordered macroarrays or microarrays of nucleic acid molecules (probes) that are complementary or substantially identical to a miRNA molecule or precursor miRNA molecules and that are positioned on a support material in a spatially separated organization. Macroarrays are typically composed of sheets of nitrocellulose or nylon upon which probes have been spotted. Microarrays can be fabricated by spotting nucleic acid molecules, e.g., genes, oligonucleotides onto substrates or fabricating oligonucleotide sequences in situ on a substrate. Spotted or fabricated nucleic acid molecules can be applied in a high density matrix pattern of up to about 30 non-identical nucleic acid molecules per square centimeter or higher, e.g., up to about 100 or even 1000 per square centimeter. Microarrays typically use coated glass as the solid support, in contrast to the nitrocellulose-based material of filter arrays. By having an ordered array of miRNA-complementing nucleic acid samples, the position of each sample can be tracked and linked to the original sample. A variety of different array devices in which a plurality of distinct nucleic acid probes are stably associated with the surface of a solid support are known to those of skill in the art. Useful substrates for arrays include nylon, glass and silicon. The arrays may vary in a number of different ways, including average probe length, sequence or types of probes, nature of bond between the probe and the array surface, e.g., covalent or non-covalent, and the like. The labeling and screening methods described herein and the arrays are not limited in its utility with respect to any parameter except that the probes detect miRNA; consequently, methods and compositions may be used with a variety of different types of miRNA arrays. In certain aspects of the disclosure, the miRNA is miR-129 consisting of the nucleic acid sequence, CUUUUUGCGGUCUGGGCUUGC (SEQ ID NO. 1). Where, A=Adenine, C=Cytosine, G=Guanine, and U=Uracil.

In one embodiment of the present disclosure, the expression of miR-129 is quantified in a biological sample relative to a reference sample (e.g., the level of miR-129 present in a corresponding control tissue from non-cancerous surgical margins or benign tissue). In another embodiment, the level of miR-129 is detected using a nucleic acid probe that specifically binds miR-129. The term, "Nucleic acid probe" is any nucleic acid molecule or fragment thereof that binds miR-129 as set forth in SEQ ID NO. 1. Such nucleic acid probes are useful for the diagnosis of colorectal cancer. In one approach, quantitative PCR methods are used to identify an increase or decrease in the expression of miR-129. Here, probes may be used to hybridize to a nucleic acid sequence derived from a subject. The specificity of the probe determines whether the probe hybridizes to a naturally occurring sequence, allelic variants, or other related sequences.

In general, the measurement of a nucleic acid molecule in a subject sample is compared with a diagnostic amount present in a reference sample. A diagnostic amount distinguishes between a colorectal cancer tissue and a control non-cancerous tissue. The skilled artisan appreciates that the particular diagnostic amount used can be adjusted to increase sensitivity or specificity of the diagnostic assay depending on the preference of the diagnostician. According to this disclosure, a decrease of expression relative to control should be at least 2%, 5%, 10%, 20%, 30%, 40%, 50%, 60%, 70%, 80%, 90%, 100%, 200% or greater, in order to diagnose colorectal cancer. In another embodiment, the reduction in expression is 0.6 fold, 0.8 fold, 1.6 fold, 2 fold, 2.1 fold, 2.2 fold, 2.3 fold, 2.4 fold, 2.5 fold, 2.6 fold, 2.7 fold, 2.8 fold, 2.9 fold, 3 fold, 4.8 fold or greater.

In one embodiment, miR-129 expression measured from the subject in question and is compared to a control value in order to determine whether or not colorectal cancer exists in the subject.

In a specific embodiment a reduction in miR-129 expression levels relative to a control sample indicates that the subject has colorectal cancer. Alternatively, when the level of miR-129 expression is elevated or equal to that of a control sample, it can be determined that the subject does not have colorectal cancer. A control value can be a pre-determined value or can be determined from a control sample side-by-side with the sample obtained from the subject in question. In a specific embodiment the control sample can be a reference sample.

In yet another embodiment, the control value is established from a control sample obtained from paired non-cancerous tissue from the subject. In certain embodiments, when the amount of miR-129 expression in the test sample is less than the amount of miR-129 expression in the non-cancerous tissue control tissue from the subject, then the subject is diagnosed as having colorectal cancer.

Methods for Determining Tumor Stage

Since the current disclosure reveals that miR-129 was expressed at various levels in fifty-five colorectal cancer samples the current disclosure utilized the level of miR-129 expression as a basis to determine the severity or stage of colorectal cancer in the subject. According to the current disclosure, when correlated with tumor grade/stage, the expression of miR-129 decreased progressively from stage one to stage four thus, the extent of the reduction in miR-129 expression relative to reference samples correlates with the stage or grade of the cancer. More specifically, when compared to the levels exhibited in non-cancerous samples or stage 1 colorectal cancer reference samples, subjects with stage 2 colorectal cancer exhibit reduced miR-129 levels. In another embodiment, the reduction in miR-129 expression levels between a test sample with stage 2 colorectal cancer and a control sample is 5-6 fold. In yet another embodiment the reduction in miR-129 expression between a stage one reference sample and a test sample with stage 2 colorectal cancer is between 0.5 and 1 fold. Additionally, the reduction of miR-129 expression increased progressively in stage 3 and stage 4 samples. More specifically, the reduction in miR-129 expression between a stage 2 reference sample and a test sample with stage 3 colorectal cancer is between 1 and 3 fold, or 2-3 fold. In another aspect the reduction in miR-129 expression between a stage 3 reference sample and a test sample with stage 4 colorectal cancer is between 0.5 and 2 fold, 1-2 fold, or 1.5-2 fold. Therefore, the present disclosure provides a method of characterizing the stage of colorectal cancer in a subject by detecting a reduction in miR-129 expression levels.

Cancer spreads through a subject by invading the normal, non-cancerous tissue surrounding the tumor, via the lymph nodes and vessels, and by blood after the tumor invades the veins, capillaries and arteries of a subject. When cancer cells break away from the primary tumor ("metastasize") secondary tumors arise throughout an afflicted subject forming metastatic lesions. Generally, there are four stages of colorectal cancer discerned by the degree by which they have metastasized. Stage zero or carcinoma in situ, whereby abnormal potentially cancerous cells are found in the mucosa (innermost layer) of the colon wall. Stage one, cancerous cells have formed in the mucosa of the colon wall and has spread to the submucosa (layer of tissue under the mucosa) and may have spread to the muscle layer of the colon wall. Stage two, is composed of three subclasses, Stage two A, wherein the cancerous tissue has spread through the muscle layer of the colon wall to the serosa (outermost layer) of the colon wall, Stage two B, whereby the tumor has spread through the serosa of the colon wall but has not spread to nearby organs, and Stage two C, wherein the cancer has spread through the serosa of the colon wall and invaded nearby organs. Stage three is also divided into three subclasses; Stage three A, where the cancer may have spread through the mucosa of the colon wall to the submucosa and muscle layer, and has spread to one to three nearby lymph nodes or tissues near the lymph nodes; or the cancer has spread through the mucosa to the submucosa and four to six nearby lymph nodes, Stage 3 B, wherein the tumor has spread through the muscle layer of the colon wall to the serosa or has spread through the serosa but not to nearby organs and the cancer has spread to one to three nearby lymph nodes or to tissues near the lymph nodes; or has spread to the muscle layer or to the serosa, and to four to six nearby lymph nodes; or has spread through the mucosa to the submucosa and may have spread to the muscle layer and has spread to seven or more nearby lymph nodes. In Stage 3 C colorectal cancer, the tumor has spread through the serosa of the colon wall but not to nearby organs and the cancer has spread to four to six nearby lymph nodes; or the cancer has spread through the muscle layer to the serosa or has spread through the serosa but not to nearby organs and the cancer has spread to seven or more nearby lymph nodes; or the cancer has spread through the serosa to nearby organs and to one or more nearby lymph nodes or to tissues near the lymph nodes. Finally, Stage four colon cancer is divided into two subclasses Stage four A, whereby the cancer has spread through the colon wall and into nearby organs and one organ that is not near the colon or to a distant lymph node, Stage 4 B is classified as, cancer that has spread through the colon wall and into nearby organs and more than one organ that is not near the colon or into the lining of the abdominal wall.

In some examples, when referring to tumor grade or stage herein (i.e., grade scale of 1-4) the tumor grading is as per the Tumor, Nodes, Metastasis classification of malignant tumors (TNM). Here, tumor describes the size of the original (primary) tumor and whether it has invaded nearby tissue, whereas N describes nearby (regional) lymph nodes that are involved, and M describes distant metastasis (spread of the cancer from an additional part of the organism).

Yet another example of tumor staging includes the Dukes classification system for colorectal cancer. Here, the stages are identified as Stage A, whereby the tumor is confined to the intestinal wall, Stage B whereby the tumor exhibits invasion through the bowel but has not invaded the lymph nodes, Stage C whereby, cancerous cells or tissue is found within the lymph nodes of a subject, and Stage D, whereby the tumor exhibits widespread metastases into several organs of the subject.

In another aspect of tumor staging the Astler Coller classification system is can be used. Here, Stage A colorectal cancer is identified as cancer that is only present in the Limited to mucosa of the intestine, Stage B1 whereby the tumor extends into muscularis propria but does not penetrate through it and the tumor has not metastasized into the lymph nodes, Stage B2 colorectal cancer is denoted by a tumor that penetrates through muscularis propria and the tumor has not metastasized into the lymph nodes, Stage C1 is characterized by a tumor that extends into muscularis propria but does not penetrate through it and the tumor has metastasized into the lymph nodes, Stage C2 colorectal cancer is classified as a tumor that penetrates through muscularis propria where the tumor has metastasized into the lymph nodes, and Stage D describes a tumor that has metastasized throughout the organism or subject.

In one embodiment the method for characterizing the stage of colorectal cancer in a subject includes detecting or measuring miR-129 in a biological sample obtained from a subject, wherein the level of miR-129 expression is reduced when compared to the level exhibited by control samples or data sets obtained from normal noncancerous patients, but is increased when compared to the level exhibited grade two colorectal cancer samples or data sets thereof, thus indicating that the subject has grade one colorectal cancer. In certain embodiments the reduction in miR-129 expression between a control sample and a sample exhibiting stage one colorectal cancer is between 3-5 fold, 4-6 fold, 5-7 fold or greater.

A biological sample is obtained from the subject in question. The biological sample that can be used in accordance with the present disclosure may be collected by a variety of means. Non-limiting examples include fine needle aspiration, surgical excision, endoscopic biopsy, excisional biopsy, incisional biopsy, fine needle biopsy, punch biopsy, shave biopsy and skin biopsy. Additionally, miR-129 expression can also be detected from cancer or tumor tissue or from other body fluid samples such as whole blood (or the plasma or serum fractions thereof) or lymphatic tissue. In some embodiments, the sample obtained from a subject is used directly without any preliminary treatments or processing, such as fractionation or extraction of DNA or RNA. In certain aspects, a tumor or tumor biopsy is obtained from a subject and fluid from the tumor is removed, e.g., by centrifugation, and the tumor fluid is used as the sample for measuring miR-129 expression levels.

After a suitable biological sample is obtained, the level of miR-129 expression in the sample can be determined using various techniques referenced herein. In certain embodiments of the current disclosure miR-129 expression may be measured by a process selected from q-RT-PCR, Northern blotting, microarray analysis, or RT-PCR.

In one aspect of the current disclosure, the stage of colorectal cancer is characterized by comparing the level of miR-129 in a biological sample to that of two or more reference samples. For example, where the level of miR-129 expression is reduced when compared to the level of miR-129 exhibited by stage one colorectal cancer reference sample or data sets thereof but, the level of miR-129 expression in the test sample is greater than that of a stage three colorectal cancer reference sample or data sets thereof, the subject can be diagnosed with stage two colorectal cancer. In certain embodiments the reduction in miR-129 expression between a stage one colorectal cancer reference sample and a sample exhibiting stage two colorectal cancer is between 0.05-10 fold, 0.5-5 fold, 0.5-2 fold, or 0.5-1 fold.

In another aspect of the current disclosure, the method for characterizing the stage of colorectal cancer in a subject includes a biological sample exhibiting a reduced level of miR-129 expression when compared to the level of miR-129 exhibited by grade two colorectal cancer reference samples or data sets thereof but, the level of miR-129 expression in the subject sample is greater than that of a grade four colorectal cancer reference sample or data sets thereof, the subject can be diagnosed with grade three colorectal cancer. In certain embodiments the reduction in miR-129 expression between a stage two colorectal cancer reference sample and a sample exhibiting stage three colorectal cancer is between 0.05-5 fold, 0.5-3 fold, or 0.5-2.5 fold.

In yet another aspect of the current disclosure, the method for characterizing the stage of colorectal cancer in a subject includes a biological sample exhibiting a reduced level of miR-129 expression when compared to the level of miR-129 exhibited by grade three colorectal cancer reference samples or data sets thereof indicates that the subject has grade four colorectal cancer. In certain embodiments the reduction in miR-129 expression between a stage three colorectal cancer reference sample and a sample exhibiting stage four colorectal cancer is between 0.05-5 fold, 0.5-3 fold, 0.5-2.0 fold or 0.5-1.6 fold.

In yet another embodiment, the method for characterizing the grade of colorectal cancer disclosed herein, may be used alone or in combination with another method of grading or staging of cancer known to one of ordinary skill in the art.

Methods for Identifying a Subject Resistent to Treatment

The intrinsic apoptosis signaling pathway for programmed cell death involves non-receptor-mediated internal cellular signals that induce mitochondria mediated apoptosis in response to cellular stresses, such as DNA damage. During instances of high cellular stress the mitochondria will release pro-apoptotic proteins such as Bax, Bak and Blk, which binds to BCL2, an anti-apototic protein that leads to the release of Cytochrome C. Cytochrome C then forms a complex with Apaf-1 that activates cysteine protease, Caspase 9 and Caspase-3. The activation of Caspase-3 then causes cell death via proteolysis. In cancerous cells the pro-apoptotic proteins are not released, apoptosis is inhibited and cells will not die, leading to tumorigenesis.

The current disclosure shows that miR-129 suppresses BCL2 expression and activity in a cell or subject resulting in an increased amount of available pro-apoptotic proteins to cleave procaspase-9 which then activates caspase-3, which then leads to increased cell death. Additionally, the current disclosure reveals that miR-129 regulates apoptosis by directly targeting BCL2 as well as by impacting other critical cell death-related proteins. For example, the data described herein shows that increasing miR-129 reduced the expression or activity of E2F3, a transcription factor protein that regulates cell cycle progression and reduced the expression or activity of thymidylate synthase (TS) protein levels, resulting in increased cellular proliferation and increased efficacy of chemotherapeutic agents.

According to the present methods, miR-129 expression is detected in a biological sample obtained from a subject, wherein a reduced level of miR-129 expression in the sample is shown, identifying the subject as resistant to chemotherapy.

A biological sample is obtained from the subject in question. The biological sample that can be used in accordance with the present disclosure may be collected by a variety of means. Non-limiting examples include fine needle aspiration, surgical excision, endoscopic biopsy, excisional biopsy, incisional biopsy, fine needle biopsy, punch biopsy, shave biopsy and skin biopsy. Additionally, miR-129 expression can be detected from cancer or tumor tissue or from other body fluid samples such as whole blood (or the plasma or serum fractions thereof) or lymphatic tissue. In one embodiment, the sample obtained from a subject is used directly without any preliminary treatments or processing, such as fractionation or extraction of DNA or RNA. In other embodiments, the sample is processed such that DNA, RNA or proteins can be extracted or enriched from the sample before detecting miR-129 expression levels. Methods of extracting DNA from biological sample are well known in the art, and may be performed using, for example, phenol/chloroform, ethanol, or commercially available DNA extraction reagents. In a specific embodiment a sample is processed by obtaining a tumor or tumor biopsy and the fluid from the tumor is removed prior to observation, e.g., by centrifugation, and the tumor fluid or tissue is used as the sample for measuring miR-129 expression levels.

After a suitable biological sample is obtained, the level of miR-129 expression in the sample can be determined using various techniques. In certain embodiments of the current disclosure miR-129 expression may be measured by a process selected from q-RT-PCR, Northern blotting, microarray analysis, or RT-PCR. In one aspect, real-time reverse transcriptase PCR is conducted, wherein a stem-loop primer is hybridized to the microRNA molecule to be detected, then reverse transcribed with reverse transcriptase enzymes, and then quantified using real-time PCR (see, e.g., Chen, C., et al. *Nucleic Acids Res.* (2005). 33(20): e179). Additional methods of isolating nucleic acid are well known in the art. See, e.g., US Patent Publication No. 2007/0054287.

As demonstrated herein, significant reductions in miR-129 expression levels have been observed in cancer samples relative to non-cancerous controls or reference samples which have been correlated to the resistance or responsiveness of the cancerous cells to treatment with a chemotherapeutic agent.

In certain embodiments, the chemotherapeutic agent is an agent that inhibits the expression or activity of BCL2, thymidylate synthase or E2F3. Certain non-limiting examples of chemotherapeutic agents include: anti-metabolites such as methotrexate and fluoropyrimidine-based pyrimidine antagonist, 5-fluorouracil (5-FU) (Carac® cream, Efudex®, Fluoroplex®, Adrucil®) and S-1; antifolates, including polyglutamatable antifolate compounds; raltitrexed (Tomudex®), GW1843 and pemetrexed (Alimta®) and non-polyglutamatable antifolate compounds; nolatrexed (Thymitaq®), plevitrexed, BGC945; folic acid analogs such as denopterin, methotrexate, pteropterin, trimetrexate; and purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine particularly those which inhibit expression of genes in signaling pathways implicated in aberrant cell proliferation or apoptosis, such as, for example, BCL2, thymidylate synthase or E2F3; and pharmaceutically acceptable salts, acids or derivatives of any of the above.

More specifically, thymidylate synthase (RefSeq: NG_028255.1, NM_001071.2, NP_001062.1) is a ubiquitous enzyme, which catalyses the essential methylation of dUMP to generate dTMP, one of the four bases which make up DNA. The reaction requires CH H$_4$-folate as a cofactor, both as a methyl group donor, and uniquely, as a reductant. The constant requirement for CH H$_4$-folate means that thymidylate synthase activity is strongly linked to the activity of the two enzymes responsible for replenishing the cellular folate pool: Dihydrofolate reductase and Serine transhydroxymethylase. Thymidylate synthase is a homodimer of 30-35 kDa subunits. The active site binds both the folate cofactor and the dUMP substrate simultaneously, with the dUMP covalently bonded to the enzyme via a nucleophilic cysteine residue (see, Carreras et al, *Annu. Rev. Biochem.*, (1995) 64:721-762).

The thymidylate synthase reaction is a crucial part of the pyrimidine biosynthesis pathway which generates dCTP and dTTP for incorporation into DNA. This reaction is required for DNA replication and cell growth. Thymidylate synthase activity is therefore required by all rapidly dividing cells such as cancer cells. Due to its association with DNA synthesis and therefore cellular replication, thymidylate synthase has been the target for anti-cancer drugs for many years. Non-limiting examples of thymidylate synthase inhibitors include, folate and dUMP analogs, such as 5-fluorouracil (5-FU).

E2F transcription factor 3, E2F3 (RefSeq NG_029591.1, NM_001243076.2, NP_001230005.1) is a transcription factor that binds DNA and interacts with effector proteins, including but not limited to, retinoblastoma protein to regulate the expression of genes involved in cell cycle regulation.

B-cell lymphoma 2 (BCL2), (RefSeq NG_009361.1, NM_000633, NP_000624) including isoform a (NM_000633.2, NP_000624.2) and β NM_000657.2, NP_000648.2 thereof, are encoded by the Bcl-2 gene, which is a member of the BCL2 family of regulator proteins that regulate mitochondria regulated cell death via the intrinsic apoptosis pathway. BCL2 is an integral outer mitochondrial membrane protein that blocks the apoptotic death of cell cells by binding BAD and BAK proteins. Non-limiting examples of BCL2 inhibitors include, antisense oligonucleotides, such as Oblimersen (Genasense; Genta Inc.), BH3 mimetic small molecule inhibitors including, ABT-737 (Abbott Laboratories, Inc.), ABT-199 (Abbott Laboratories, Inc.), and Obatoclax (Cephalon Inc.).

In one embodiment, miR-129 expression measured from the subject in question is compared to a reference value or control in order to determine whether or not the subject will likely be responsive to treatment with a chemotherapeutic agent. To assess the relative level of miR-129 expression, the level of miR-129 expression in a cancerous tissue sample obtained from the subject can be subjected to one or more comparisons. In general, it can be compared to: (a) miR-129 expression level(s) in normal, non-cancerous tissue from the organ in which the cancer originated (e.g., colon, intestine, lymph node); (b) miR-129 expression levels in a collection of cancer tissue samples which have been characterized as responsive to chemotherapeutic agents, including 5-FU, other fluoropyrimidines or antifolate compounds; (c) miR-129 expression level(s) in a collection of normal, non-cancerous tissue samples; or (d) miR-129 expression level(s) in an arbitrary standard. A reference value/sample or control value can be a pre-determined value or can be determined from a control sample side by side with the sample obtained from the subject in question. In a specific embodiment, the control value is established from a control sample obtained from normal or benign tissue, for example, benign tissue of the organ or subject from which the cancer originated.

According to the current disclosure, the amount of miR-129 expression in a test sample is analyzed and compared to the level of miR-129 expression from a control sample (e.g., a sample from benign tissue or surgical margins), and the difference in miR-129 expression levels between the test sample and the control can be determined. A reduction in the level of miR-129 expression is evidenced by a significant decrease in miR-129 expression of a test sample relative to a control, which indicates that the test subject is not likely to be responsive to chemotherapy.

Non-limiting examples of a significant reduction in miR-129 expression levels, include but are not limited to, 2%, 3%, 4%, 5%, 6%, 7%, 8%, 9%, 10%, 15%, 20%, 30%, 40%, 50%, 60%, 70%, 80%, 90%, 100%, 200%, 300%, 400% or more, under that of a control sample. In certain embodiments, a significant reduction is miR-129 expression is between 0.5 and 5.0 fold, 1.0 fold and 4.0 fold, between 1.0 fold and 3.0 fold, or 0.5 fold 0.6 fold, 0.8 fold, 1.6 fold, 2 fold, 2.1 fold, 2.2 fold, 2.3 fold, 2.4 fold, 2.5 fold, 2.6 fold, 2.7 fold, 2.8 fold, 2.9 fold, 3 fold, 4.8 fold or greater.

Classification of patients based on miR-129 expression levels not only predicts the patient's responsiveness to chemotherapy, but also permits personalized design of treatment options. For example, for subjects identified as having miR-129 expression levels that are reduced or equal to that of a control level, chemotherapy is not expected to be effective and should not be administered alone. However, these subjects can be treated with an agent as described herein that sensitizes a subject to chemotherapy. For subjects identified as having miR-129 expression levels that are equal to or elevated relative to control, the subjects will likely be responsive to chemotherapy and chemotherapy should be administered. In a further embodiment, the chemotherapy used in the prescribed method is a fluoropyrimidine or antifolate compound including, but not limited to, 5-FU.

The analysis of miR-129 expression can occur before or after a cancer diagnosis has been made and prior to, during or after the initiation of treatment with a chemotherapeutic agent. In another aspect, the analysis of miR-129 expression occurs after a cancer diagnosis has been made. In yet another aspect of the current disclosure, the analysis of miR-129 expression occurs with or after the initiation of treatment with a fluoropyrimidine or antifolate based therapeutic agent. In yet another aspect the analysis of miR-129 expression occurs after said cancer has been determined to be resistant to treatment with a chemotherapeutic agent.

Therapeutic Methods

The current disclosure shows that miR-129 directly interacts with BCL-2, TS and E2F2 by acting as a pro-apoptotic microRNA to enhance the sensitivity of a tumor to chemotherapy. Additionally, the present disclosure utilizes human cancer cell lines and tumor xenografts models to show that increasing miR-129 expression levels using isolated nucleic acids increased the sensitivity of colorectal cancer cells to chemotherapeutic agents, such as 5-FU by inducing cell cycle arrest and inhibition of cell proliferation. In other embodiments, isolated miR-129 nucleic acid molecules alone are shown to reduce the size of tumors by targeting colorectal cancer stem cells. Thus, the disclosure further provides a method of treating cancer in a subject who has been identified as exhibiting a reduced level of miR-129 expression or activity, by administering to the subject an effective amount of an agent that inhibits expression or activity of BCL2, TS, or E2F3 or effectors thereof. In another embodiment the inhibition of expression of BCL2 sensitizes the cancer to the chemotherapeutic treatment.

In one embodiment of the current disclosure, the agent that inhibits BCL2 is a nucleic acid, a small molecule, an antibody or a peptide, any of which directly or indirectly inhibits the expression or anti-apoptotic activity of BCL2.

In some embodiments, the BCL2 inhibitor is an isolated nucleic acid that modulates the level of BCL2 expression in the subject being treated. In a specific embodiment, the isolated nucleic acid is a short hairpin RNA (shRNA), siRNA, or nucleic acid complementary to a portion of the BCL2 3'UTR. Non-limiting examples of said isolated nucleic acids of the current disclosure include nucleic acid sequences that bind to nucleotide sequence CAAAAA, or a portion thereof, or an isolated nucleic acid that is substantially identical to or contains the nucleotide sequence GUUUUU.

In specific embodiments, a BCL2 inhibitor is administered to a subject before, during (including concurrently with), or after the treatment with a chemotherapeutic agent.

In other embodiments, an additional therapeutic agent is provided to the subject including administration of a chemotherapeutic agent independent of a BCL2 inhibitor, and radiation, among others.

In the context of a combination therapy (i.e., involving a BCL2, E2F3 or TS inhibitor such as miR-129 in combination with a chemotherapeutic compound, and optionally another independent chemotherapeutic agent), the agent may be administered before, during, or after commencing therapy with a chemotherapeutic compound, or an additional chemotherapeutic agent, as well as any combination thereof.

The data described herein show that miR-129 suppressed the protein expression of TS, a critical target in cellular proliferation, providing an explanation for the synergy of 5-FU with miR-129 agents.

In one embodiment of the current disclosure, the agent that inhibits TS is a nucleic acid, a small molecule, an antibody or a peptide, any of which directly or indirectly inhibits the expression or biological activity of TS.

In certain embodiments, a TS inhibitor useful in the current methods is an isolated nucleic acid that modulates the level of TS expression in the subject being treated. In a specific embodiment, the isolated nucleic acid is a short hairpin RNA (shRNA), siRNA, or nucleic acid complementary to a portion of the TS protein or RNA. A non-limiting example of an isolated nucleic acid of the current disclosure includes an isolated nucleic acid that is substantially identical to SEQ ID NO. 1.

In specific embodiments, a TS inhibitor is administered to a subject before, during (including simultaneously with), or after the treatment with a chemotherapeutic agent.

In other embodiments, an additional therapeutic agent is provided to the subject including administration of a chemotherapeutic agent independent of a TS inhibitor, and another chemotherapeutic agent and/or radiation.

In the context of a combination therapy (i.e., involving a TS inhibitor in combination with a chemotherapeutic compound, and optionally another independent chemotherapeutic agent), the TS inhibitor may be administered before, during, or after commencing therapy with a chemotherapeutic compound, or an additional chemotherapeutic agent, as well as any combination thereof, i.e., before and during, before and after, during and after, or before, during and after commencing the additional chemotherapeutic treatment.

E2F3 is a transcription factor which regulates cell-cycle progression. Here, E2F3 protein expression was quantified after miR-129 transfection by Western immunoblot analysis revealing that miR-129 was able to reduce E2F3 levels and increase cytotoxicity of chemotherapeutic agents, such as 5-FU.

In one embodiment of the current disclosure, the agent that inhibits E2F3 is a nucleic acid, a small molecule, an antibody or a peptide, any of which directly or indirectly inhibits the expression or biological activity of TS.

In certain embodiments, an E2F3 inhibitor useful in the current methods is an isolated nucleic acid that modulates the level of E2F3 expression in the subject being treated. In a specific embodiment, the isolated nucleic acid is a short hairpin RNA (shRNA), siRNA, or nucleic acid complementary to a portion of the E2F3 protein or RNA. A non-limiting example of an isolated nucleic acid of the current disclosure includes an isolated nucleic acid that is substantially identical to SEQ ID NO. 1.

In specific embodiments, an E2F3 inhibitor is administered to a subject before, during (including simultaneously with), or after the treatment with a chemotherapeutic agent.

In other embodiments, an additional therapeutic agent is provided to the subject including administration of a chemotherapeutic agent independent of an E2F3 inhibitor, and another chemotherapeutic agent and/or radiation.

In the context of a combination therapy (i.e., involving a E2F3 inhibitor in combination with a chemotherapeutic compound, and optionally another independent chemotherapeutic agent), the E2F3 inhibitor may be administered before, during, or after commencing therapy with a chemotherapeutic compound, or an additional chemotherapeutic agent, as well as any combination thereof, i.e., before and during, before and after, during and after, or before, during and after commencing the additional chemotherapeutic treatment.

In another aspect of the current disclosure, the ability of a chemotherapeutic agent or an agent that inhibits, BCL2, E2F3 or TS for use with the current methods can be determined using pharmacological models well know in the art for example, cytotoxic assays, apoptosis staining assays, xenograft assays and binding assays.

A non-limiting example includes the measurement of propidium iodide and Annexin V to determine ctyotoxicity of a compound by measuring cellular apoptosis.

Phosphatidylserine is located on the cytoplasmic/internal side of the cell membrane. Conversely, during apoptosis phosphatidylserine is localized on the extracellular side of the plasma membrane, expositing phosphatidylserine to the external environment and making it a readily detectable antigen for annexin V conjugated fluorescent dyes. Annexin V is a calcium-dependent phospholipid-binding protein that has a high affinity for phosphatidylserine and thus, can be used to quantitatively determine the percentage of cells within a population that are undergoing apoptosis. Flourescent annexin V dye can then be detected by flow cytometry with or without propidium iodide staining.

Propidium iodide is widely used in conjunction with Annexin V to determine if cells are viable, apoptotic, or necrotic by detecting alterations in plasma membrane integrity and permeability that occur during apoptosis. The ability of propidium iodide to enter a cell is dependent upon the permeability of the cellular membrane as propidium iodide membrane will not be present in healthy cells because the cellular membrane remains intact until later in apoptotic process. In late apoptotic cells, the integrity of the plasma and nuclear membranes decreases, allowing propidium iodide to pass through the membranes, and incorporate into nucleic acids within the cell.

Taken together, cells treated with a target compound, which stain positive for annexin V and negative for propidium iodide are undergoing apoptosis and thus, the target compound may be a useful chemotherapeutic agent. Cells that stain positive for both annexin V and propidium iodide are either in the end stage of apoptosis, are undergoing necrosis, or are already dead. Cells that stain negative for both FITC annexin V and propidium iodide are alive and not undergoing measurable apoptosis.

A suitable therapeutic agent of the current disclosure may be administered within a pharmaceutically-acceptable diluents, carrier, or excipient, in unit dosage form. As described herein, if desired, treatment with an isolated nucleic acid molecule of the current disclosure may be combined with therapies such as, for example, radiotherapy, surgery, among others.

The dosage of an agent that is administered to a subject in need thereof may vary, depending on the reason for use and the individual subject. The dosage may be adjusted based on the subject's weight, the age and health of the subject, and tolerance for the agent.

The amount of an agent of the current disclosure to be used depends on many factors. Dosages may include about 2 mg/kg of bodyweight/day, about 5 mg/kg of bodyweight/day, about 10 mg/kg of bodyweight/day, about 15 mg/kg of bodyweight/day, about 20 mg/kg of bodyweight/day, about 25 mg/kg of bodyweight/day, about 30 mg/kg of bodyweight/day, about 40 mg/kg of bodyweight/day, about 50 mg/kg of bodyweight/day, about 60 mg/kg of bodyweight/day, about 70 mg/kg of bodyweight/day, about 80 mg/kg of bodyweight/day, about 90 mg/kg of bodyweight/day, about 100 mg/kg of bodyweight/day, about 125 mg/kg of bodyweight/day, about 150 mg/kg of bodyweight/day, about 175 mg/kg of bodyweight/day, about 200 mg/kg of bodyweight/day, about 250 mg/kg of bodyweight/day, about 300 mg/kg of bodyweight/day, about 350 mg/kg of bodyweight/day, about 400 mg/kg of bodyweight/day, about 500 mg/kg of bodyweight/day, about 600 mg/kg of bodyweight/day, about 700 mg/kg of bodyweight/day, about 800 mg/kg of bodyweight/day, and about 900 mg/kg of bodyweight/day. Routine experimentation may be used to determine the appropriate value for each patient by monitoring the compound's effect on miR-129 expression levels or activity or BCL2 levels or activity, or TS levels or activity, or E2F3 levels or the disease pathology, which can be frequently and easily monitored. The agent can be administered once or multiple times per day. The frequency of administration may vary from a single dose per day to multiple doses per day. Routes of administration include oral, intravenous and intraperitoneal, but other forms of administration may be chosen as well.

The effective amount of an agent according to the present disclosure may be administered along any of the routes commonly known in the art. This includes, for example, (1) oral administration; (2) parenteral administration, for example, by subcutaneous, intramuscular or intravenous injection; (3) topical administration; or (4) intravaginal or intrarectal administration; (5) sublingual or buccal administration; (6) ocular administration; (7) transdermal administration; (8) nasal administration; and (9) administration directly to the organ or cells in need thereof.

The effective amount of an agent according to the present disclosure may be formulated together with one or more pharmaceutically acceptable excipients. The active ingredient and excipient(s) may be formulated into compositions and dosage forms according to methods known in the art. These compositions and dosage forms may be specially formulated for administration in solid or liquid form, including those adapted for the following: (1) oral administration, for example, tablets, capsules, powders, granules, pastes for application to the tongue, aqueous or non-aqueous solutions or suspensions, drenches, or syrups; (2) parenteral administration, for example, by subcutaneous, intramuscular or intravenous injection as, for example, a sterile solution or suspension; (3) topical application, for example, as a cream, ointment or spray applied to the skin, lungs, or mucous membranes; or (4) intravaginally or intrarectally, for example, as a pessary, cream or foam; (5) sublingually or buccally; (6) ocularly; (7) transdermally; or (8) nasally.

The phrase "pharmaceutically acceptable" is employed herein to refer to those compounds, materials, compositions, and/or dosage forms which are, within the scope of sound medical judgment, suitable for use in contact with the tissues of the subject with toxicity, irritation, allergic response, or other problems or complications, commensurate with a reasonable benefit/risk ratio.

The phrase "pharmaceutically-acceptable excipient" as used herein refers to a pharmaceutically-acceptable material, composition or vehicle, such as a liquid or solid filler, diluent, carrier, manufacturing aid (e.g., lubricant, talc magnesium, calcium or zinc stearate, or stearic acid), solvent or encapsulating material, involved in carrying or transporting the therapeutic compound for administration to the subject. Each excipient should be "acceptable" in the sense of being compatible with the other ingredients of the formulation and not injurious to the subject. Some examples of materials which can serve as pharmaceutically-acceptable excipients include: sugars, such as lactose, glucose and sucrose; starches, such as corn starch and potato starch; cellulose and its derivatives, such as sodium carboxymethyl cellulose, ethyl cellulose and cellulose acetate; gelatin; talc; waxes; oils, such as peanut oil, cottonseed oil, safflower oil, sesame oil, olive oil, corn oil and soybean oil; glycols, such as ethylene glycol and propylene glycol; polyols, such as glycerin, sorbitol, mannitol and polyethylene glycol; esters, such as ethyl oleate and ethyl laurate; agar; buffering agents; water; isotonic saline; pH buffered solutions; and other non-toxic compatible substances employed in pharmaceutical formulations. If desired, certain sweetening and/or flavoring and/or coloring agents may be added. Other suitable excipients can be found in standard pharmaceutical texts, e.g. in "Remington's Pharmaceutical Sciences", The Science and Practice of Pharmacy, 19$^{th}$ Ed. Mack Publishing Company, Easton, Pa., (1995).

Excipients are added to the agent for a variety of purposes. Diluents increase the bulk of a solid pharmaceutical composition, and may make a pharmaceutical dosage form containing the composition easier for the patient and caregiver to handle. Diluents for solid compositions include, for example, microcrystalline cellulose (e.g. Avicel®), microfine cellulose, lactose, starch, pregelatinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g. Eudragit®), potassium chloride, powdered cellulose, sodium chloride, sorbitol and talc.

Solid pharmaceutical agents that are compacted into a dosage form, such as a tablet, may include excipients whose functions include helping to bind the active ingredient and other excipients together after compression. Binders for solid pharmaceutical compositions include acacia, alginic acid, carbomer (e.g. carbopol), carboxymethylcellulose sodium, dextrin, ethyl cellulose, gelatin, guar gum, hydrogenated vegetable oil, hydroxyethyl cellulose, hydroxypropyl cellulose (e.g. Klucel®), hydroxypropyl methyl cellulose (e.g. Methocel®), liquid glucose, magnesium aluminum silicate, maltodextrin, methylcellulose, polymethacrylates, povidone (e.g. Kollidon®, Plasdone®), pregelatinized starch, sodium alginate and starch.

The dissolution rate of a compacted solid pharmaceutical composition in the subject's stomach may be increased by the addition of a disintegrant to the composition. Disintegrants include alginic acid, carboxymethylcellulose calcium, carboxymethylcellulose sodium (e.g. Ac-Di-Sol®, Primellose®), colloidal silicon dioxide, croscarmellose sodium, crospovidone (e.g. Kollidon®, Polyplasdone®), guar gum, magnesium aluminum silicate, methyl cellulose, microcrystalline cellulose, polacrilin potassium, powdered cellulose, pregelatinized starch, sodium alginate, sodium starch glycolate (e.g. Explotab®) and starch.

Glidants can be added to improve the flowability of a non-compacted solid agent and to improve the accuracy of dosing. Excipients that may function as glidants include colloidal silicon dioxide, magnesium trisilicate, powdered cellulose, starch, talc and tribasic calcium phosphate.

When a dosage form such as a tablet is made by the compaction of a powdered composition, the composition is subjected to pressure from a punch and dye. Some excipients and active ingredients have a tendency to adhere to the surfaces of the punch and dye, which can cause the product to have pitting and other surface irregularities. A lubricant can be added to the composition to reduce adhesion and ease the release of the product from the dye. Lubricants include magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc and zinc stearate.

In liquid pharmaceutical compositions of the present disclosure, the agent and any other solid excipients are dissolved or suspended in a liquid carrier such as water, water-for-injection, vegetable oil, alcohol, polyethylene glycol, propylene glycol or glycerin. Liquid pharmaceutical compositions may contain emulsifying agents to disperse uniformly throughout the composition an active ingredient or other excipient that is not soluble in the liquid carrier. Emulsifying agents that may be useful in liquid compositions of the present invention include, for example, gelatin, egg yolk, casein, cholesterol, acacia, tragacanth, chondrus, pectin, methyl cellulose, carbomer, cetostearyl alcohol and cetyl alcohol. Liquid pharmaceutical compositions of the present disclosure may also contain a viscosity enhancing agent to improve the mouth-feel of the product and/or coat the lining of the gastrointestinal tract. Such agents include acacia, alginic acid bentonite, carbomer, carboxymethylcellulose calcium or sodium, cetostearyl alcohol, methyl cellulose, ethylcellulose, gelatin guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth and xanthan gum.

Sweetening agents such as sorbitol, saccharin, sodium saccharin, sucrose, aspartame, fructose, mannitol and invert sugar may be added to improve the taste. Flavoring agents and flavor enhancers may make the dosage form more palatable to the patient. Common flavoring agents and flavor enhancers for pharmaceutical products that may be included in the composition of the present disclosure include maltol, vanillin, ethyl vanillin, menthol, citric acid, fumaric acid, ethyl maltol and tartaric acid.

Preservatives and chelating agents such as alcohol, sodium benzoate, butylated hydroxy toluene, butylated hydroxyanisole and ethylenediamine tetraacetic acid may be added at levels safe for ingestion to improve storage stability.

According to the present disclosure, a liquid composition may also contain a buffer such as gluconic acid, lactic acid, citric acid or acetic acid, sodium gluconate, sodium lactate, sodium citrate or sodium acetate. Selection of excipients and the amounts used may be readily determined by the formulation scientist based upon experience and consideration of standard procedures and reference works in the field.

Solid and liquid compositions may also be dyed using any pharmaceutically acceptable colorant to improve their appearance and/or facilitate patient identification of the product and unit dosage level.

The dosage form of the present disclosure may be a capsule containing the composition, for example, a powdered or granulated solid composition of the disclosure, within either a hard or soft shell. The shell may be made from gelatin and optionally contain a plasticizer such as glycerin and sorbitol, and an opacifying agent or colorant.

A composition for tableting or capsule filling may be prepared by wet granulation. In wet granulation, some or all of the active ingredients and excipients in powder form are blended and then further mixed in the presence of a liquid, typically water, that causes the powders to clump into granules. The granulate is screened and/or milled, dried and then screened and/or milled to the desired particle size. The granulate may then be tableted, or other excipients may be added prior to tableting, such as a glidant and/or a lubricant. A tableting composition may be prepared conventionally by dry blending. For example, the blended composition of the actives and excipients may be compacted into a slug or a sheet and then comminuted into compacted granules. The compacted granules may subsequently be compressed into a tablet.

As an alternative to dry granulation, a blended composition may be compressed directly into a compacted dosage form using direct compression techniques. Direct compression produces a more uniform tablet without granules. Excipients that are particularly well suited for direct compression tableting include microcrystalline cellulose, spray dried lactose, dicalcium phosphate dihydrate and colloidal silica. The proper use of these and other excipients in direct compression tableting is known to those in the art with experience and skill in particular formulation challenges of direct compression tableting.

A capsule filling may include any of the aforementioned blends and granulates that were described with reference to tableting; however, they are not subjected to a final tableting step.

EXAMPLES

The following examples further illustrate the disclosure, but should not be construed to limit the scope of the disclosure in any way.

Example 1. BCL2 is a Direct Target of miR-129 in Colorectal Cancer Cells

The current disclosure identifies a putative miR-129 binding site, CAAAAA at nucleotide position 1525-1530 in the 3'-UTR of Bcl2 mRNA using TargetScan analysis (FIG. 1a). The controlled expression of BCL2 by miR-129 was demonstrated by the transfection of three colorectal cancer cell lines, HCT116, RICO and SW480 with either negative control miRNA or miR-129 and protein expression of BCL2 was quantified by Western immunoblot analysis. siRNA against BCL2 (siBCL2) was used as a positive control. These data show that miR-129 reduced the BCL2 protein expression in all cell lines tested compared to the negative control miRNA (FIG. 1b). To further confirm the direct interaction between miR-129 and BCL2 mRNA, the miR-129 binding site was cloned from BCL2 mRNA into a luciferase reporter vector (FIG. 1a) and co-transfected with either negative control miRNA or miR-129 into HCT116 cells, and the luciferase activity was measured. Data revealed that miR-129 significantly inhibited the luciferase activity compared with the negative control miRNA (FIG. 1c), showing that miR-129 interacts directly with the 3'-UTR of BCL2 mRNA. In addition, miR-129 did not inhibit the luciferase activity of the reporter vector containing 3'-UTR of BCL2 with three point mutations in the miR-129 binding site (FIGS. 1a and c). Thus, miR-129 specifically suppresses BCL2 protein synthesis in colorectal cancer cells.

To fully understand the impact of miR-129 on apoptotic and other cell death pathways, 84 genes involved in cell death pathways were quantified via real time qRT-PCR analysis comparing miR-129 transfected cells with negative miRNA transfected control cells. The results show a significant down-regulation in BCL2 mRNA expression levels, a finding consistent with the Western immunoblot analysis. Moreover, a significant difference in other apoptosis related targets was observed, including but not limited to, those molecules acting in the intrinsic apoptosis pathway (Table 1). These data show that miR-129 regulates apoptosis by directly targeting BCL2 as well as by impacting other critical cell death-related proteins.

Example 2. miR-129 Promotes Apoptosis in Colorectal Cancer Cells

Figure 2:
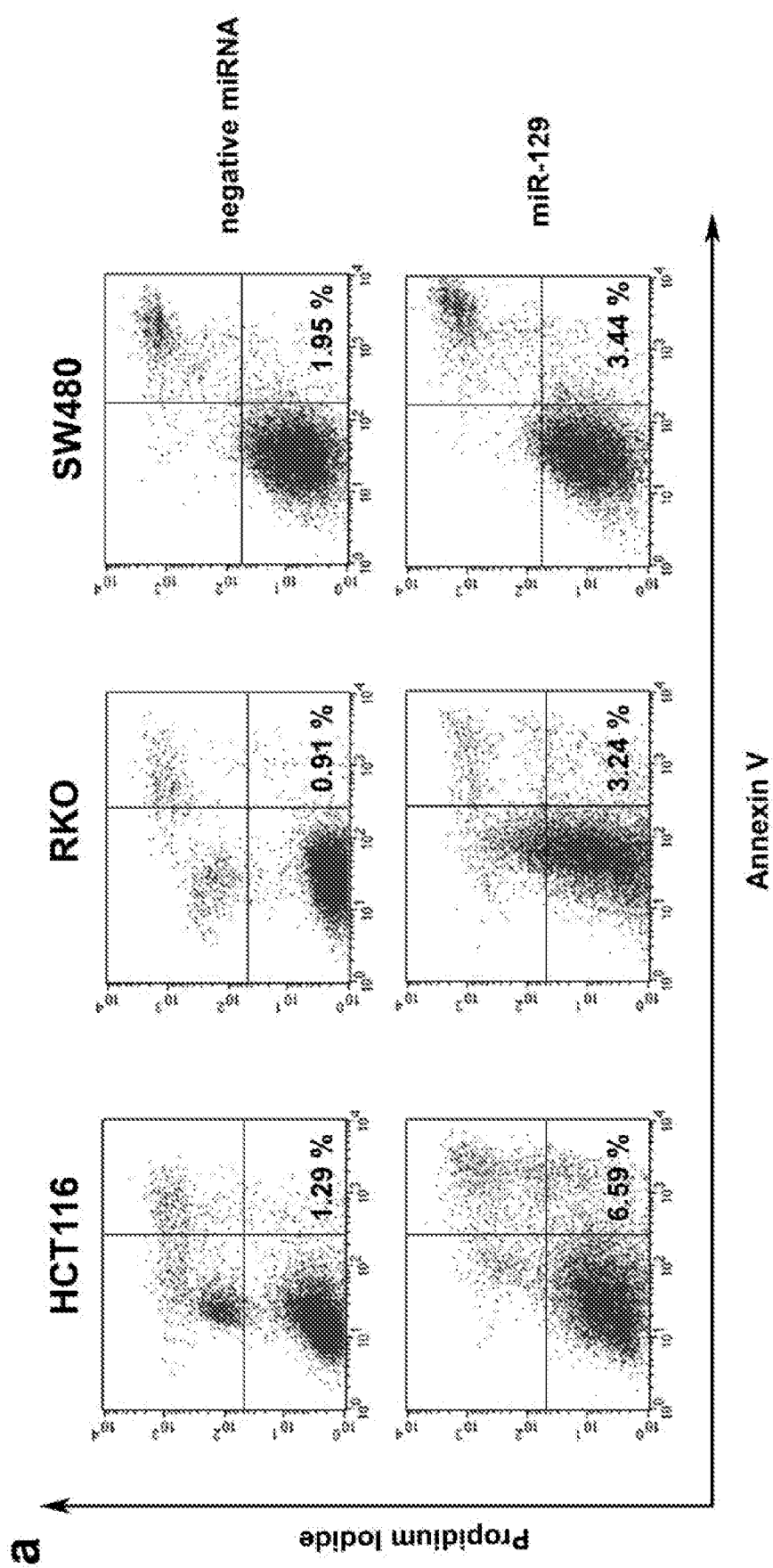
FIG. 2. miR-129 positively regulates apoptosis. (a) HCT116, RKO and SW480 cells were transfected with either miR-129 or negative miRNA, and stained with Annexin V and propidium iodide (PI) after 48 h. The representative apoptosis pattern was shown and, the apoptotic cells (Annexin V positive, PI negative) were indicated as the percentage of gated cells. Quantitative analysis of apoptosis was shown in (b). (c) Western immunoblot analysis was performed for cleaved caspase-3 and cleaved caspase-9 in HCT116 cells with ectopic expression of miR-129 (n=3).
Figure 2:
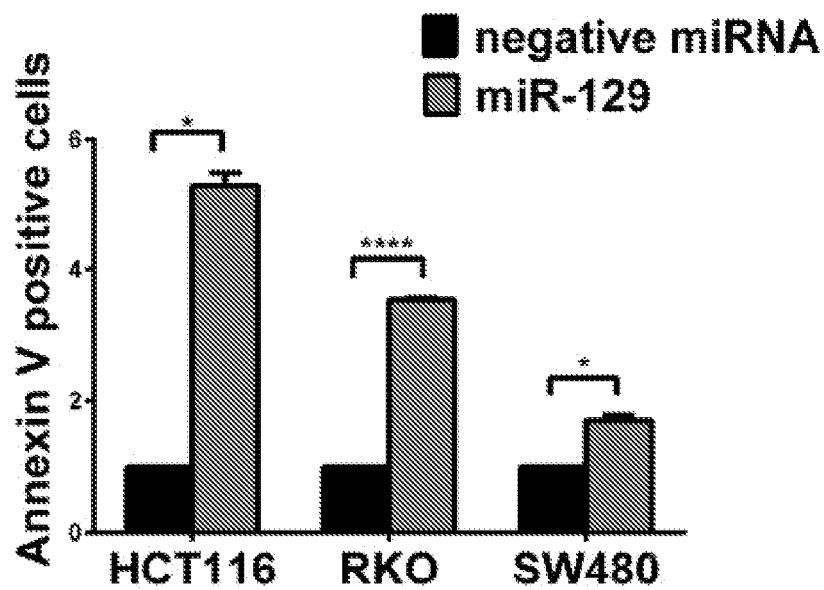
Figure 2:
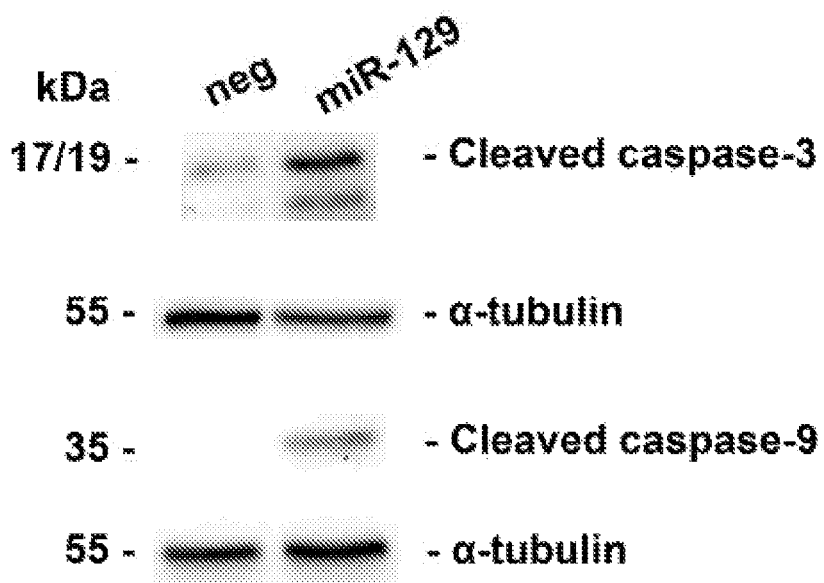

BCL2 is an anti-apoptotic gene involved in an evolutionarily conserved intrinsic apoptosis pathway. To identify the biological effects of BCL2 repression by miR-129, a FACS analysis was conducted to quantify apoptosis via annexin V and propidium iodide staining. The results show that the presence of miR-129 increased apoptosis significantly in all colorectal cancer cell lines tested, as assessed by the proportion of cells that are annexin V positive and propidium iodide negative (FIGS. 2a and b). Next, it was determined that the increase in apoptosis was due to the activation of the intrinsic apoptosis pathway because the quantified protein expression of cleaved caspase-9 and cleaved caspase-3 by Western immunoblot analysis revealed that, miR-129 elevated the protein levels of both cleaved caspase-9 and -3 (FIG. 2c). These data show that miR-129 functions as a pro-apoptotic molecule by directly targeting BCL2.

Figure 3:
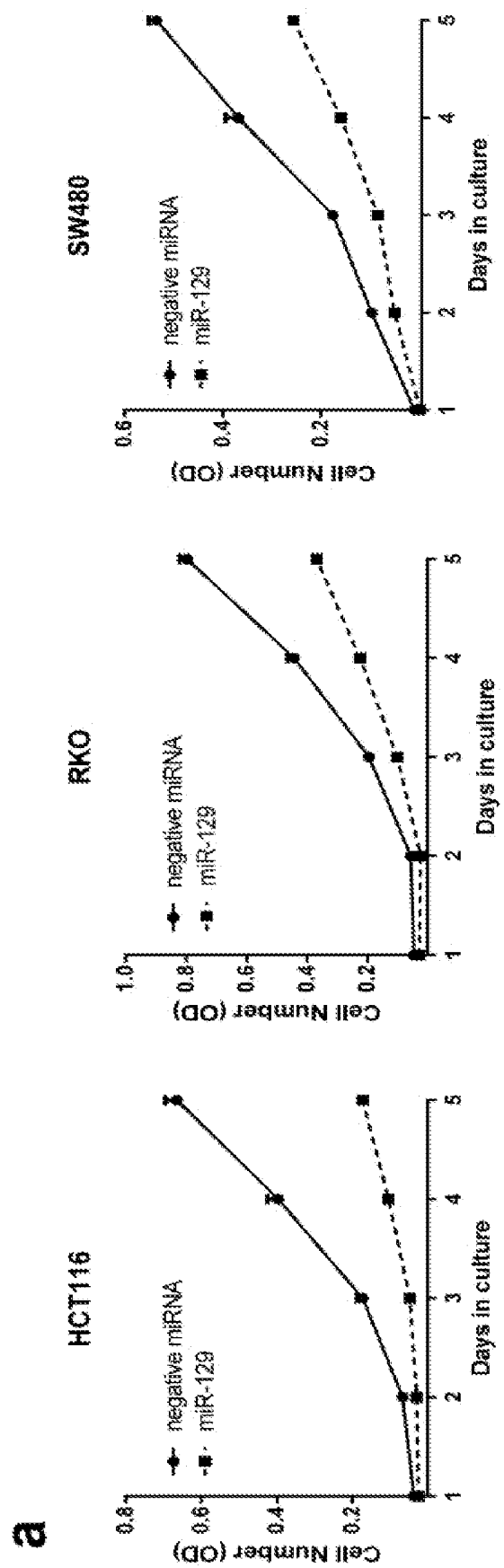
FIG. 3. miR-129 suppresses colorectal cancer cell growth and induces cell cycle arrest. (a) HCT116, RICO and SW480 cells were transfected with either miR-129 or negative miRNA, and cell numbers were measured with WST-1 assay at days 1, 3 and 5. Cell cycle analysis was performed to determine the impact of miR-129. The representative flow cytometry pattern was shown in (b) and the G1/S and G2/S ratios were shown in (c) (n=3). (d) Colon cancer stem cells, i.e., CD133$^{+HI}$CD44$^{+HI}$ cells were subcutaneously injected into NOD/SCID mice ($1\times10^4$ cells). Mice were treated with either (top left) control lentiviral GFP vector and lentiviral miR-129 expressing construct (n=5) or (top right) mice were injected with negative miRNA (n=5) or miR-129 precursor (n=5) at 1.25 nmol per injection. Tumor sizes were then analyzed 7 weeks after initial treatment (lentiviral or injection). Representative images of mice bearing tumors at week 7 exhibit a significant reduction is tumor size (mm2) in mice treated with miR-129 when compared to mice treated with control (i.e., vector or negative miRNA). Scale bar: 1 cm. (bottom left) Quantitative analysis of colon cancer stem cells in tumor xenografts transfected with lentiviral miR-129 or control constructs reveal a significant reduction in tumor size. (bottom right) Quantitative analysis of colon cancer stem cells in tumor xenografts transfected with control and miR-129 precursor RNA.
Figure 3:
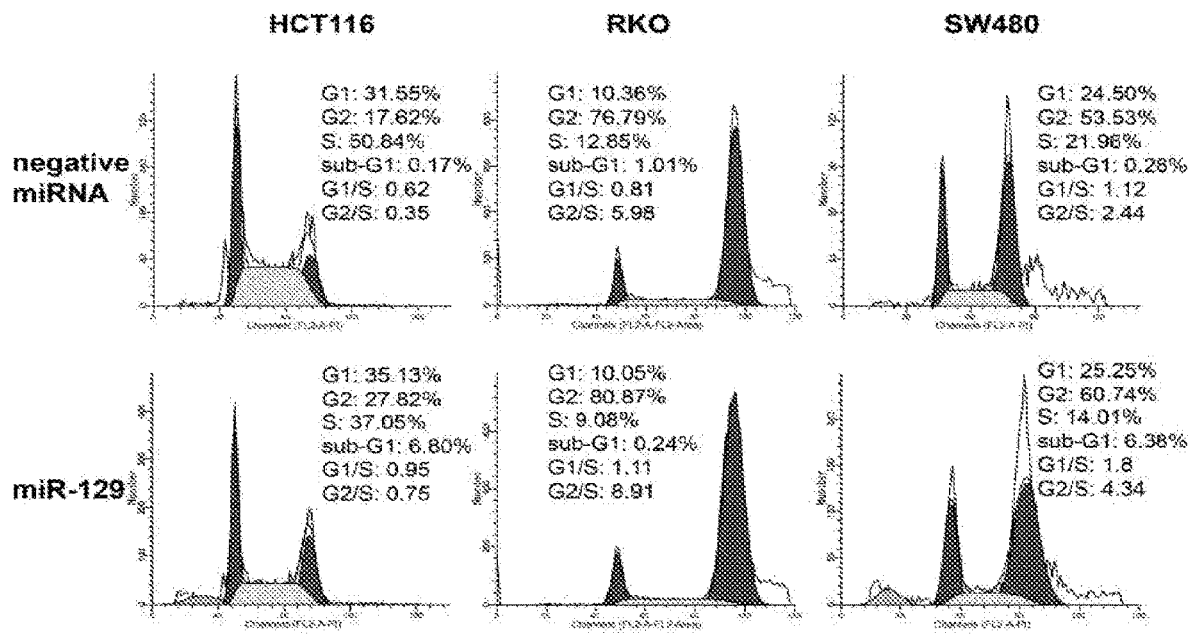
Figure 3:
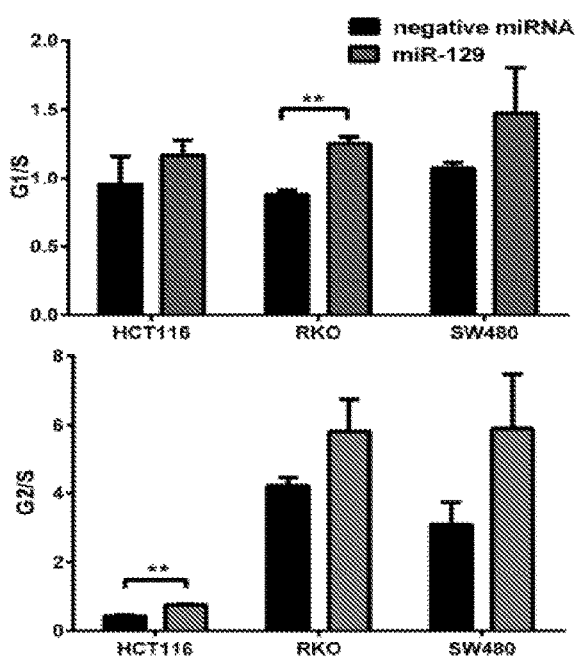
Figure 3:
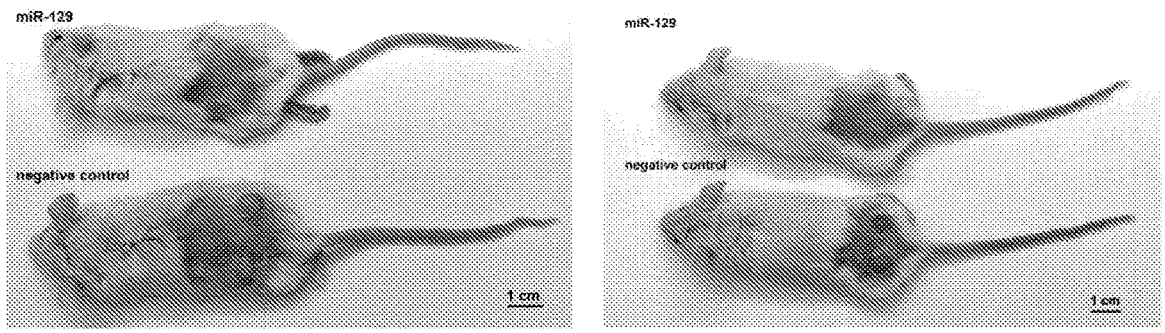
Figure 3:
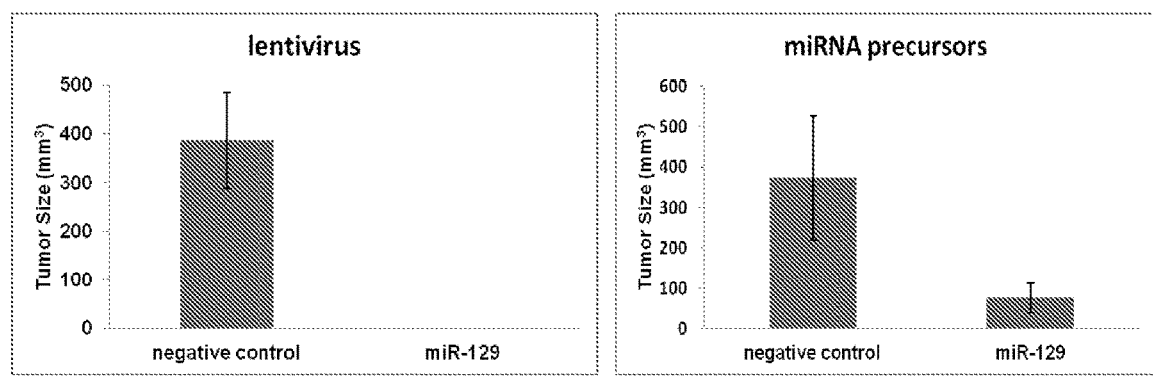

Example 3. Overexpression of miR-129 Inhibited Colorectal Cancer Cell Growth In Vitro and In Vivo The impact of miR-129 on cell proliferation and cell cycle was analyzed by comparing colorectal cancer cells overexpressing miR-129 with control cells not expressing miRNA. Cell proliferation was significantly inhibited in the presence of miR-129 (FIG. 3a). At day 5, the cell proliferation of miR-129 expressing HCT116, RKO and SW480 cells were reduced by 41.2%, 43.9% and 44.7% when compared to the negative controls, respectively. Thus, the overexpression of miR-129 triggered cell cycle arrest in both G1 and/or G2 phase (FIG. 3b). G1/S and G2/S ratios indicated that the cell cycle arrest reached significance at G2 checkpoint in HCT116 cells, and at G1 checkpoint in RKO cells (FIG. 3c). Furthermore, FIG. 3d, shows that injection of miR-129 or delivery of miR-129 via viral vector reduces tumor size significantly by directly inhibiting colorectal cancer stem cells in a xenograph mouse model. These results reveal that miR-129 inhibits cell proliferation and induces cell cycle arrest in colorectal cancer cells and can be used as a therapeutic agent for subjects having colorectal cancer.

Example 4. miR-129 Enhanced the Cytotoxicity of 5-FU In Vitro

Figure 4:
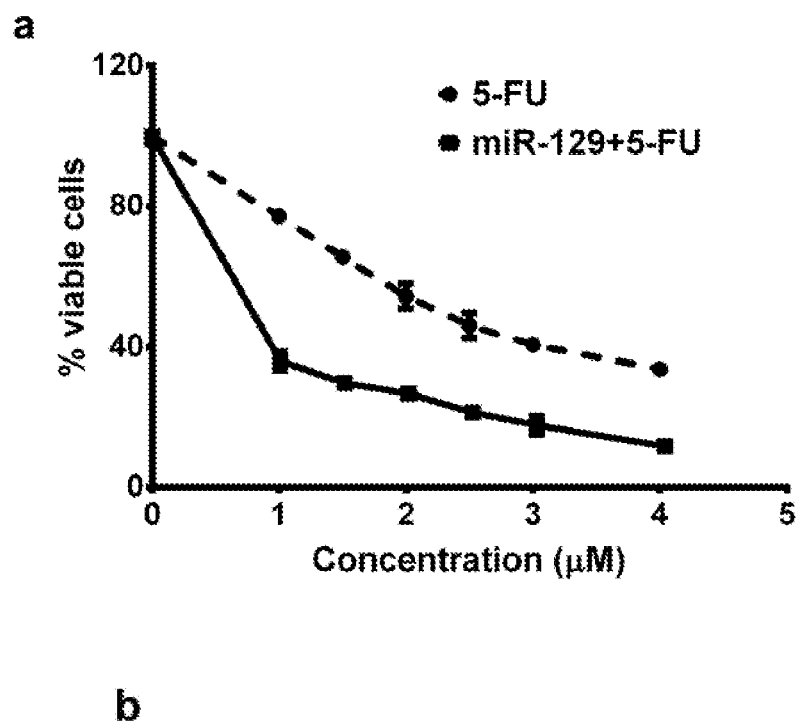
FIG. 4. miR-129 functions synergistically with 5-FU in vitro. (a) The inhibitory effects of 5-FU on the growth of HCT116 cells alone or in combination with miR-129 were observed by a WST-1 assay. (b) The combination effects of 5-FU and miR-129 were determined by calculating the combination index (CI) values for each data point in (a). CI<1 indicates a synergistic effect. (c) $IC_{50}$ values were determined based on the 50% growth inhibition using WST-1 assay. (d) Western immunoblot analysis was performed for TS and E2F3 protein levels in HCT116 cells with ectopic expression of miR-129.
Figure 4:
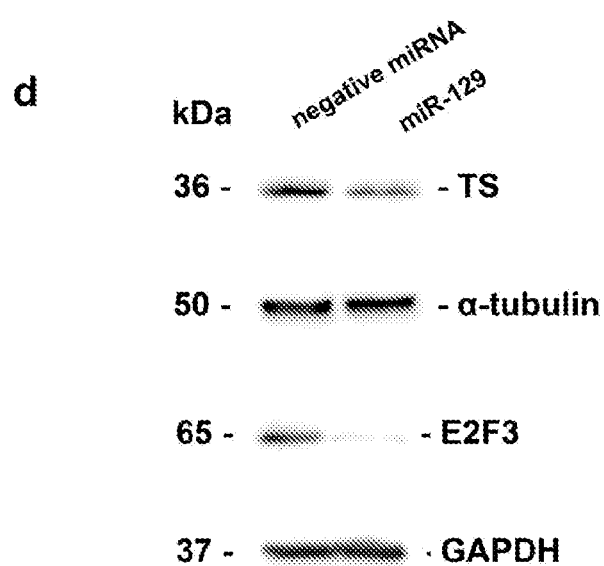

Based on the profound effect of miR-129 on proliferation and apoptosis, the impact of miR-129 on the most widely used chemotherapy drug in colorectal cancer, 5-fluorouracil (5-FU) was examined. Here, HCT116 cells were treated with either precursor miR-129 or 5-FU or a combination of miR-129 and 5-FU (at a fixed ratio 1:10) for 72 hours. Then, a concentration-dependent curve was developed based on the cell viability of cells treated with 5-FU alone or the cell viability of those treated with the miR-129 and 5-FU combination. This demonstrated a significant increase in cell death in the combined treatment compared to 5-FU treatment alone (FIG. 4a). To determine whether combination of miR-129 with 5-FU was synergistic, the combination index (CI) for each combination treatment in FIG. 4a was calculated according to the methods previously described in Chou, T-C et al., *CompuSyn Software for Drug Combinations and for General Dose-Effect Analysis, and User's*

*Guide*. Paramus, N.J. ComboSyn, Inc.; 2007. Here, CI<1, CI=1, and CI>1 indicate synergistic, additive, and antagonistic effects, respectively. The data showed that the CI values were <1 in all combinations tested (FIG. 4b). Finally, the effects of combination treatment on IC50 values were illustrated in FIG. 4c. The $IC_{50}$ values for miR-129 and 5-FU were 11.2 nM and 2.3 µM, respectively. When combined, $IC_{50}$ values for miR-129 and 5-FU decreased to 6.3 nM and 0.6 µM, respectively (FIG. 4C). Taken together, these results reveal that miR-129 exerts a strong synergistic effect with 5-FU on limiting the growth of colorectal cancer cells, and thus, miR-129 expression is useful as an adjuvant therapy for the treatment of colorectal cancer.

Next, since miR-129 functioned as a therapeutic agent with 5-FU and because TS was one of the predicted targets of miR-129 based on the TargetScan analysis, the effect of miR-129 on TS protein levels, a 5-FU target was analyzed. The results revealed that miR-129 suppressed the protein expression of TS, providing an explanation for the synergy of 5-FU with miR-129 (FIG. 4d). Moreover, E2F3 is a transcription factor which regulates cell-cycle progression, thus E2F3 protein expression was quantified after miR-129 transfection by Western immunoblot analysis. Results revealed that miR-129 was able to reduce E2F3 protein levels (FIG. 4d). Therefore, the instant methods show that miR-129 acts on several critical genes that regulate apoptosis, proliferation, and the cell cycle, which leads to an anti-proliferative/apoptotic phenotype, and ultimately enhanced chemosensitivity.

Example 5. miR-129 Enhanced the Cytotoxicity of 5-FU In Vivo

Figure 5:
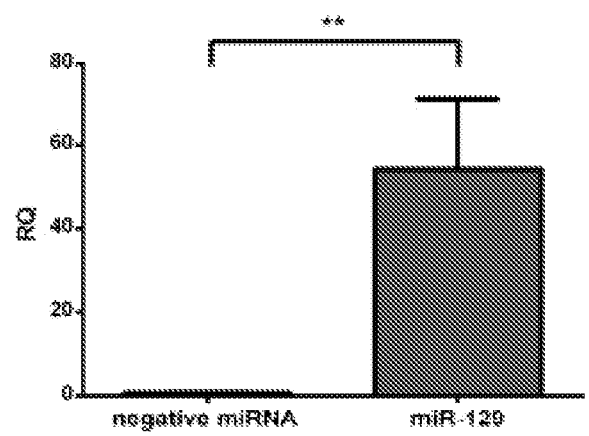
FIG. 5. miR-129 enhances the cytotoxicity of 5-FU in vivo. (a) Expression level of miR-129 in tumor xenografts was quantified by real-time qRT-PCR and miR-129 injected tumors had significantly higher levels of miR-129 than the negative controls (n=3, P<0.01). (b) HCT116 cells were subcutaneously injected into NOD/SCID mice. On days 14, 17 and 20 (indicated by arrows), mice were treated with either negative miRNA (n=6) or miR-129 precursor (n=5) or 5-FU alone (n=5) or 5-FU and miR-129 together (n=5), and tumor sizes were measured during the treatment until day 24 when mice were sacrificed. (c) Representative images of mice bearing HCT116 tumors at day 24 were shown. Arrows indicate the subcutaneous tumors. Scale bar: 2 cm.
Figure 5:
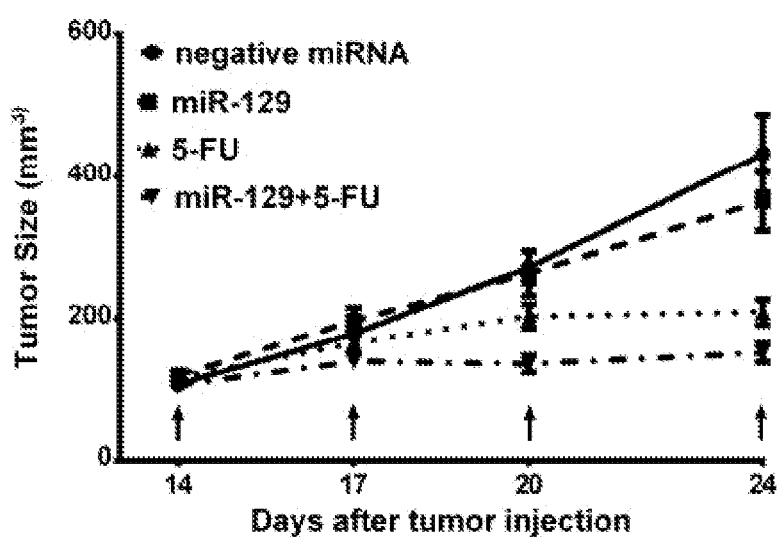
Figure 5:
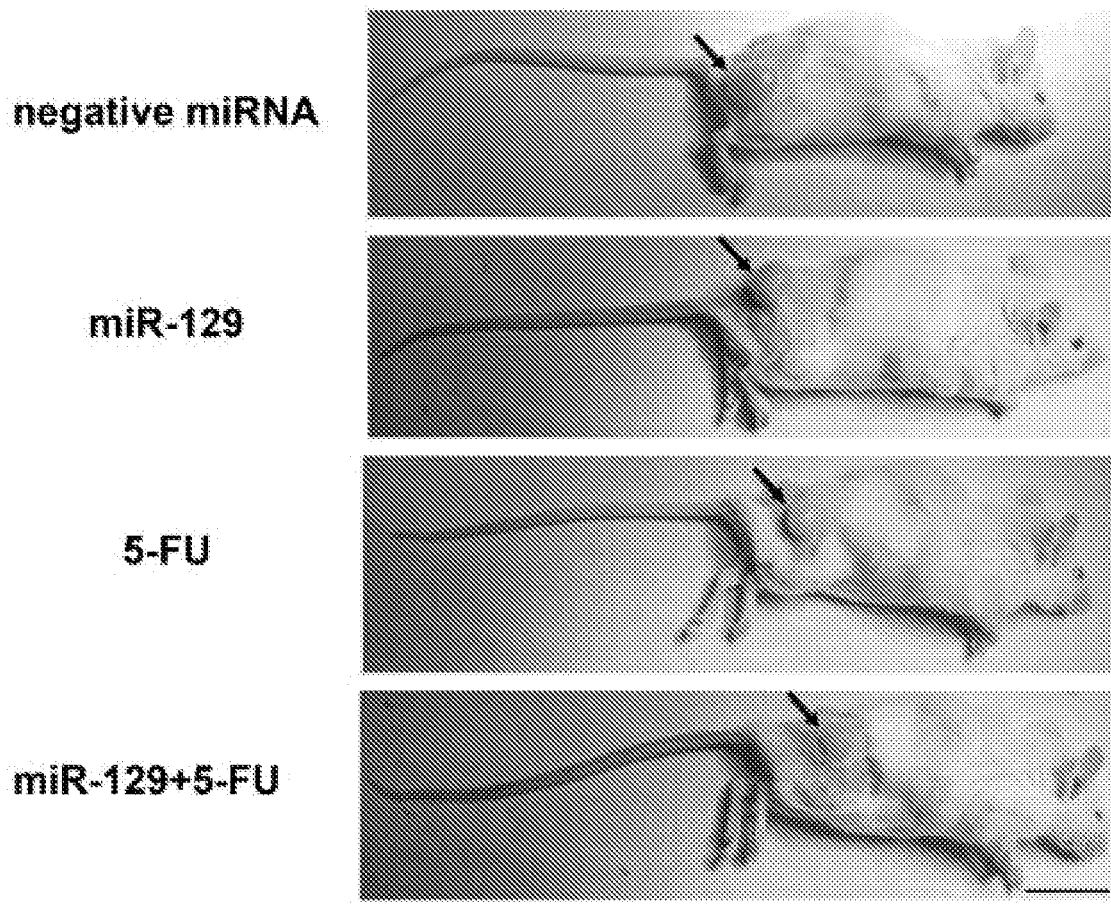

To further demonstrate that in vivo delivery of miR-129 increases the cytotoxicity of 5-FU, a mouse colorectal tumor xenograft model was established by subcutaneously inoculating $2.5 \times 10^6$ HCT116 cells (with 50% matrigel) in NOD/SCID mice. When solid and palpable tumors with an average volume of 100-150 mm³ were formed (at day 14), mice were randomly separated into four groups such that each group was treated either with negative control miRNA, miR-129 alone, 5-FU alone or miR-129 and 5-FU together. The miRNAs were complexed with siPORTamine and injected intratumorally while 5-FU (50 µg g$^{-1}$) was injected systemically via the tail vein. All injections were provided in 3-day intervals for a total of three times before the tumors were collected at day 24. Notably, either unmodified synthetic miRNAs or isolated microRNA can be used with the current methods. Here, the expression levels of miR-129 in tumor xenografts after sacrifice were quantified by real time qRT-PCR analysis and it was found that miR-129 injected tumors had an approximately 70 fold increase in miR-129 levels compared with the negative control group (FIG. 5a), which indicates that delivery of miR-129 into the tumors was successful. Importantly, despite the overexpression, the expression levels of miR-129 copy number remained within the physiological range (less than 20 copies/cell based on cycle threshold value at 30, which is equal to the expression of miR-129 in normal colon mucosa). Moreover, the control tumor xenografts had no miR-129 expression (cycle threshold value at 35). These results demonstrated that treatment with miR-129 alone sufficiently reduced tumor size and 5-FU treatment alone induced a strong inhibitory effect (P<0.01, at day 24) compared with negative miRNA. Unexpectedly, when miR-129 was combined with 5-FU, it caused greater inhibition of tumor growth than 5-FU treatment alone (P<0.001, at day 24) or treatment with miR-129 alone as the average volume of miR-129 treated, 5-FU treated or miR-129 and 5-FU treated tumors was ~84.4%, 48.4%, and 35.4% of the control group at day 24, respectively (FIG. 5b). Images of tumor-bearing mice at day 24 were also shown in FIG. 5c. Taken together, these results clearly show that miR-129 can be used as a stand alone therapy for colorectal cancer or can be used an adjuvant therapeutic agent that enhances the effectiveness of 5-FU on tumor growth in vivo.

Example 6. miR-129 was Down-Regulated in Human Colorectal Tumor Tissues

Figure 6:
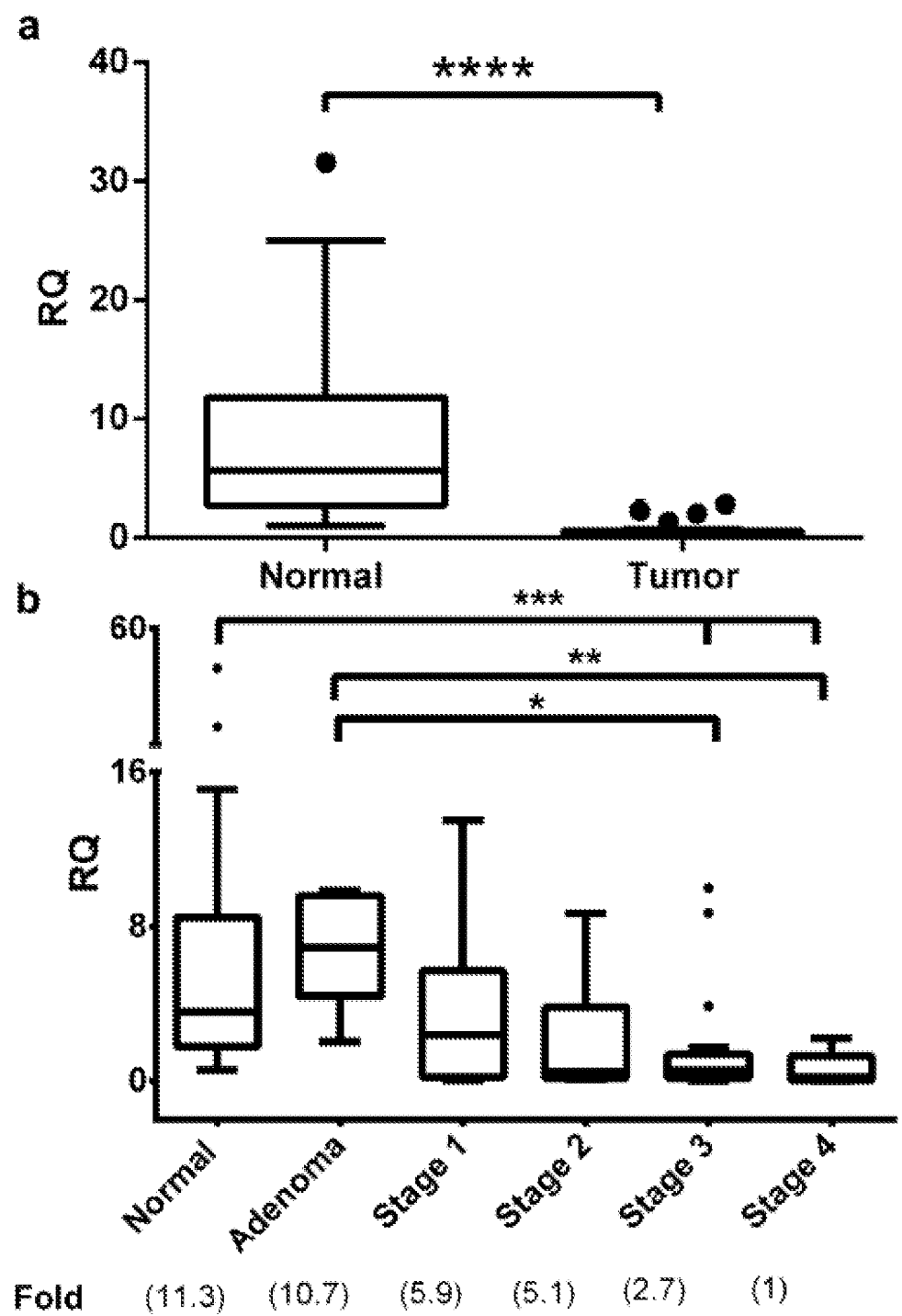
FIG. 6. miR-129 is down-regulated in CRC clinical samples. (a) Expression level of miR-129 was quantified by real-time qRT-PCR in paired tumor and normal tissues from CRC patients, and normalized to the internal control RNU44 (P<0.0001). Statistical significance was calculated by Wilcoxon matched-pairs signed rank test. (b) Expression of miR-129 in normal and tumor tissues from different stages of CRC was demonstrated. Statistical significance was calculated by Kruskal-Wallis One Way ANOVA test (P<0.0001) with Dunn's multiple comparisons test. (c) Prognostic significance of miR-129 in 20 patients with stage III colorectal cancer by Kaplan-Meier survival analysis (Log rank test, cut-off value=2.70-fold increase in miR-129 expression over that of the control sample).
Figure 6:
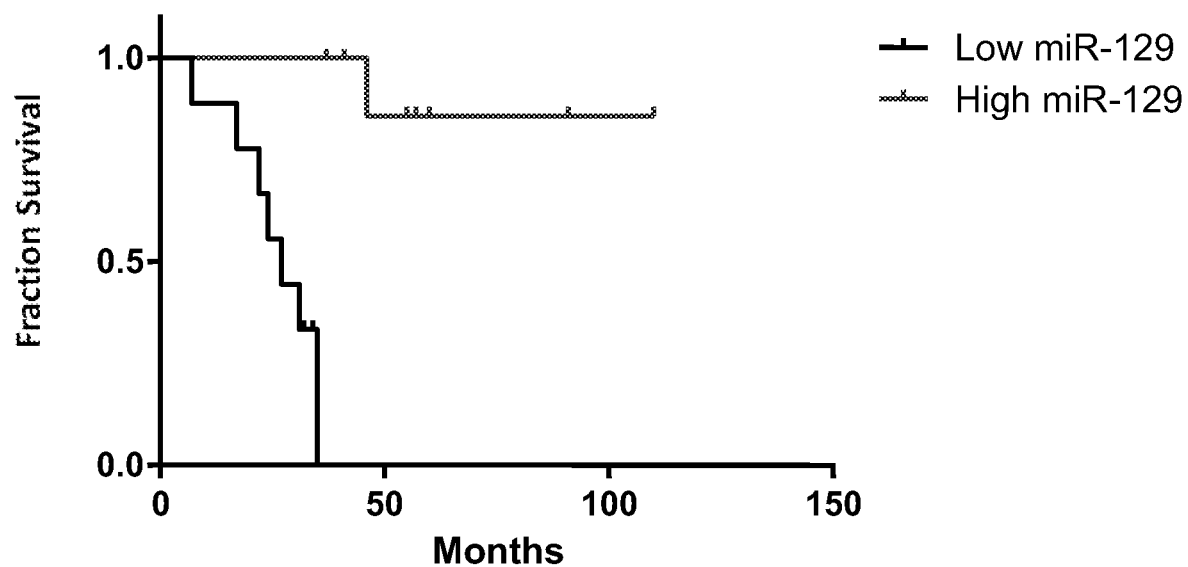

To directly demonstrate the clinical significance of miR-129, the expression levels of miR-129 from twenty-two paired fresh frozen human colorectal tumor tissues and normal controls were profiled using real time qRT-PCR analysis. The expression of miR-129 was significantly decreased in tumor tissues compared with normal controls (P<0.0001) (FIG. 6a). To evaluate the impact of miR-129 in colorectal cancer progression, the expression of miR-129 from another set of fifty-five archival tumor and normal formalin-fixed paraffin-embedded (FFPE) colorectal tumor specimens were profiled. The levels of miR-129 in colorectal cancer patients with different stages of the disease were presented in FIG. 6b revealing that the expression of miR-129 was significantly reduced in patients with stage 2, stage 3, and stage 4 of the disease compared with the normal tissues; whereas this reduction was absent in patients with stage 1 colorectal cancer. Based on these results, the decreased levels of miR-129 are associated with the progression of colorectal cancer.

Taken together, miR-129 expression is decreased in colorectal cancer and miR-129 promotes apoptosis via the suppression of BCL2. miR-129 suppresses the protein expression of TS and E2F3 which impact cellular proliferation and cell cycle progression, thus increasing apoptosis, decreasing proliferation and modulating cell cycle arrest cause an inhibitory effect on the growth of tumor cells and thereby leads to enhanced chemosensitivity.

Example 7. Materials and Methods

Cell culture. The human CRC cell line HCT116 was maintained in McCoy's 5A medium (Gibco Laboratories, Frederick, Md., USA). The other human CRC cell lines RKO and SW480 were purchased from the American Type Culture Collection (ATCC, Manassas, Va., USA), and were maintained in DMEM medium (Gibco Laboratories). All media were supplemented with 10% fetal bovine serum (Sigma-Aldrich, St Louis, Mo., USA).

Subject samples. Two clinical sample cohorts were used for this study approved by the Institution Review Board. Patient consent forms were obtained from each patient according to institutional policies. The first cohort consisted of twenty-two colorectal cancer patients who underwent surgical resection of primary tumors at the Department of Visceral and Transplantation Surgery, University of Ulm, Germany. Each patient sample contained a pair of snap-frozen specimens from normal colorectal mucosa and tumor. The second cohort consisted of fifty-five patients with primary colorectal cancer who underwent surgery at the Stony Brook University Hospital, Stony Brook, N.Y. Formalin-fixed paraffin-embedded (FFPE) tissues (twenty-one normal, nine stage 1, nine stage 2, fourteen stage 3 and two stage 4) were acquired from the archival collections of the Department of Pathology.

miRNA and siRNA Transfection.

HCT116, RKO and SW480 cells were plated in 6-well plates at $2\times10^5$, $1\times10^5$ and $1\times10^5$ per well, respectively. Twenty-four hours after plating, 100 nM of miR-129 precursor (Ambion, Carlsbad, Calif., USA) or siRNA against BCL2 (Dharmacon, Lafayette, Colo., USA) were transfected to the cells with oligofectamine (Invitrogen, Carlsbad, Calif., USA) in accordance with the manufacturer's protocol. Negative miRNA (Ambion) was also transfected as a negative control.

Western Immunoblot Analysis.

Forty-eight hours after transfection, cells were lysed with RIPA buffer (Sigma-Aldrich), and Western immunoblotting was performed using standard procedures. The primary antibodies used for the analysis were mouse anti-human BCL2 antibody (1:200; Thermo Fisher Scientific, Fremont, Calif., USA), rabbit anti-human cleaved caspase-3 antibody (1:200; Cell Signaling Technology, Beverly, Mass., USA), rabbit anti-human cleaved caspase-9 antibody (1:200; Cell Signaling Technology), mouse anti-human E2F3 antibody (1:5000; Millipore, Billerica, Mass., USA), mouse anti-human TS antibody (1:400; Millipore), mouse anti-human GAPDH antibody (1:1000, Santa Cruz Biotechnology, Santa Cruz, Calif., USA) or mouse anti-human α-tubulin antibody (1:1000; Millipore). Horseradish peroxidase-conjugated (HRP) antibodies against mouse (1:5000; Bio-rad, Hercules, Calif., USA) or against rabbit (1:5000; Cell Signaling Technology) were used as the secondary antibodies. HRP activity was detected with SuperSignal West Pico Chemiluminescent Substrate (Thermo Fisher Scientific) and visualized in an UVP Bioimaging system.

Luciferase Assay.

The predicted miR-129 binding sequence (wild-type, underlined) or a mismatch sequence (mutant, italic underlined) in the 3'UTR of Bcl2 mRNA were synthesized with SpeI and PmeI restriction site overhangs (Invitrogen). After annealing, double strand oligonucleotides were inserted into the pMIR-REPORT plasmid (Invitrogen), downstream of the firefly luciferase reporter. The sequences of these synthesized oligonucleotides are:

```
Forward wild-type:
                                (SEQ ID NO. 2)
5'-CTAGTTCACTGTAGTTTGGTTTTATTTGAAAACCTGACAAA
AAAAAGTTCCAGGT-3';

Reverse wild-type:
                                (SEQ ID NO. 3)
5'-AAACACCTGGAACTTTTTTTTGTCAGGTTTTCAAATAAAA
CCAAACTACAGTGA-3';

Forward mutant:
                                (SEQ ID NO. 4)
5'-CTAGTTCACTGTAGTTTGGTTTTATTTGAAAACCTGATAGA
CAAAAAGTTCCAGGT-3';

Reverse mutant:
                                (SEQ ID NO. 5)
5'-AAACACCTGGAACTTTTTGTCTATCAGGTTTTCAAATAAAA
CCAAACTACAGTGA-3'.
```

Twenty-four hours before transfection, $1.5\times10^4$ cells were plated in 96-well plate. 10 nM of miR-129 or negative miRNA was transfected into cells together with 100 ng of pMIR-REPORT-3'-UTR-BCL2 (wild-type or mutant) and 1 ng of Renilla luciferase plasmid pRL-SV40 (Promega, Madison, Wis., USA) by DharmaFect Duo (Dharmacon, Lafayette, Colo., USA) following the manufacturer's protocol. Luciferase assay was performed 24 hour after transfection by dual-luciferase reporter assay system (Promega). For each sample, firefly luciferase activity was normalized to Renilla luciferase activity and the inhibition by miR-129 was normalized to the control miRNA.

Cell Death PathwayFinder PCR Array.

RNAs were extracted from cells transfected with either precursor miR-129 or negative miRNA using TRIzol reagent (Invitrogen) in accordance with the manufacturer's protocol. RNAs were transcribed to first-strand cDNA using the $RT^2$ First Strand Kit (SABiosciences, Qiagen, Venlo, Netherlands). Next, the cDNA is mixed with $RT^2$ SYBR Green Mastermix (SABiosciences), and this mixture is aliquoted into the wells of the Cell Death PathwayFinder PCR Array (PAHS-212Z). Applied Biosytems 7500 Real-Time PCR machine was used for qRT-PCR, and relative expression values were determined using the $\Delta\Delta CT$ method.

Apoptosis Assay.

Forty-eight hours after transfection, cells were harvested, stained with propidium iodide and anti annexin-V antibody (Annexin V-FITC Apoptosis Detection kit, BD Biosciences, San Jose, Calif., USA) following the manufacturer's protocol, and stained cells were detected by flow cytometry. The experiments for the apoptosis assay were performed at least three times.

Cell Proliferation Assay.

Twenty-four hours after transfection, cells were seeded in 96-well plates at a density of 2000 cells per well. The cell proliferation assay was performed on days 1, 3 and 5 by incubating 10 μl WST-1 (Roche Applied Science, Mannheim, Germany) in the culture medium for 1 h and reading the absorbance at 450 and 630 nm. The cell proliferation rate was calculated by subtracting the absorbance at 450 nm from the absorbance at 630 nm. Experiments for the cell proliferation assay were performed at least three times.

Cell Cycle Analysis.

Thirty-six hours after transfection, cells were harvested and resuspended at 0.5 to $1\times10^6$ cells/m in modified Krishan buffer supplemented with 0.02 mg/ml RNase H (Invitrogen) and 0.05 mg/ml propidium iodide (Sigma-Aldrich, St. Louis, Mo., USA) (See, Krishan A. The Journal of Cell Biology. 1975; 66(1):188-93). Stained cells were detected by flow cytometry and results were analyzed with Modfit LT™ software. The experiments for cell cycle analysis were performed at least three times.

5-FU Treatment and Cytotoxicity Assay.

Twenty-four hours after transfection, HCT116 cells were plated in 96-well plates at $2\times10^3$ cells per well in triplicates in 100 μl of medium. After 24 hours, fresh medium containing 5-FU alone (ranged from 1 to 4 μM) or miR-129 precursor alone (ranged from 10 nM to 40 nM) or 5-FU and miR-129 together (at a constant ratio 1:10, with increasing concentrations of both compounds) were added, and cells were cultured for an additional 72 hours. Cell viability was measured using the WST-1 assay, and concentration-dependent curves were generated based on the cell viability. The combination index was calculated by CompuSyn software. See, Chou T C et al. (2007).

Colorectal Cancer Xenografts.

Ten-twelve week old NOD/SCID mice (Jackson Laboratories, Bar Harbor, Mass., USA) were used for tumor implantation. All animal procedures were approved by the Stony Brook University Institutional Animal Care and Use Committee (IACUC). The tumor implantation and miRNA injection protocol was modified from Trang et al. (see Trang P., et al., *Oncogene*. (2010) 29(11):1580-7). The mice were anesthetized by isoflurane inhalation. HCT116 cells were subcutaneously injected into the lower back areas of the mice using $2.5 \times 10^6$ cells in 100 µl McCoy's 5A with 50% matrigel (BD Biosciences). The tumor size was measured using a caliper and tumor volume was calculated using the formula V=length×width$^2$/2. When tumor volumes reach 100-150 mm$^3$ at day 14 post-injection, the mice were randomly assigned into four groups. For the first two groups, 10 µM negative miRNA or miR-129 precursor (Ambion) complexed with 1.6 µl siPORTAmine (Ambion) in 50 µl McCoy's 5A was injected into the tumors every three days. For the third group, 5-FU (Sigma-Aldrich) was injected at 50 µg/g via the tail vein every three days. Finally, for the last group, both miR-129 precursor and 5-FU were injected as described above. The mice were euthanized on day 24 post-injection by $CO_2$ inhalation, and tumors were dissected out for RNA isolation.

RNA Isolation.

For mouse xenografts, sectioned tissues were deparaffinized, hydrated and digested with proteinase K (Sigma-Aldrich) respectively. Subsequently, total RNA was isolated using the TRIzol reagent (Invitrogen). Total RNA was also isolated from clinical specimens by the TRIzol-based approach.

Real-time qRT-PCR Analysis of miR-129 Expression.

The miR-129 specific primer and the internal control RNU44 gene were purchased from Ambion. cDNA synthesis was performed by the High Capacity cDNA Synthesis Kit (Applied Biosystems, CA, USA) with miRNA specific primers. Real-time qRT-PCR was carried out on an Applied Biosytems 7500 Real-Time PCR machine with miRNA specific primers by TaqMan Gene Expression Assay (Applied Biosystems). Expression level of miR-129 was calculated by the ΔΔCT method based on the internal control RNU44, normalized to the control group and plotted as relative quantification (RQ).

Statistical Analysis.

All statistical analyses were performed with Graphpad Prism (version 6.01) software. The statistical significance between two groups was determined by Wilcoxon matched-pairs signed rank test for clinical samples and by Student's unpaired t-test for all other experiments. The statistical significance among several groups was analyzed by Kruskal-Wallis One Way Analysis of Variance (ANOVA) test with Dunn's multiple comparisons test. Data were expressed as mean±standard error of the mean (SEM). The statistical significance is either described in figure legends, or indicated with asterisks (*). *=$P<0.05$; =$P<0.01$; *=$P<0.001$; ****=$P<0.0001$.

We claim:

1. A method of treating colorectal cancer in a subject, comprising:
   (a) obtaining a biological sample from the subject;
   (b) determining that said biological sample has decreased levels of miR-129 expression;
   (c) administering to the subject an effective amount of exogenous miR-129 as set forth in SEQ ID NO:1; and
   (d) administering a therapeutic agent that reduces the level of E2F transcription factor 3 (E2F3) in the subject.

2. The method of claim 1, wherein said therapeutic agent comprises an isolated nucleic acid.

3. The method of claim 1, further comprising administering an effective amount of a second therapeutic agent, wherein reducing the level of E2F3 sensitizes said cancer to treatment with said second therapeutic agent.

4. The method of claim 3, wherein said second therapeutic agent is a chemotherapeutic agent.

5. The method of claim 4, wherein the chemotherapeutic agent is selected from the group consisting of 5-fluorouracil and S-1.

6. The method of claim 1, wherein the agent that reduces the level of E2F3 increases apoptosis.

7. The method of claim 1, wherein said biological sample is selected from the group consisting of whole blood, tissue, lymph node, and a combination thereof.

* * * * *

```
SEQUENCE LISTING

<160> NUMBER OF SEQ ID NOS: 7

<210> SEQ ID NO 1
<211> LENGTH: 21
<212> TYPE: DNA
<213> ORGANISM: Homo sapiens

<400> SEQUENCE: 1
cuuuuugcgg ucugggcuug c                                            21

<210> SEQ ID NO 2
<211> LENGTH: 56
<212> TYPE: DNA
<213> ORGANISM: Artificial Sequence
<220> FEATURE:
<223> OTHER INFORMATION: Forward primer for wild-type BCL2 microRNA
      binding domain

<400> SEQUENCE: 2
ctagttcact gtagtttggt tttatttgaa aacctgacaa aaaaaaagtt ccaggt       56

<210> SEQ ID NO 3
<211> LENGTH: 55
<212> TYPE: DNA
<213> ORGANISM: Artificial Sequence
<220> FEATURE:
<223> OTHER INFORMATION: Reverse primer for wild-type BCL2 microRNA
      binding domain

<400> SEQUENCE: 3
aaacacctgg aactttttt ttgtcaggtt ttcaaataaa accaaactac agtga         55

<210> SEQ ID NO 4
<211> LENGTH: 56
<212> TYPE: DNA
<213> ORGANISM: Artificial Sequence
<220> FEATURE:
<223> OTHER INFORMATION: Forward primer for mutant BCL2 microRNA
      binding domain
```

```
<400> SEQUENCE: 4
ctagttcact gtagtttggt tttatttgaa aacctgatag acaaaaagtt ccaggt       56

<210> SEQ ID NO 5
<211> LENGTH: 55
<212> TYPE: DNA
<213> ORGANISM: Artificial Sequence
<220> FEATURE:
<223> OTHER INFORMATION: Reverse primer for mutant BCL2 microRNA
      binding domain

<400> SEQUENCE: 5
aaacacctgg aacttttttgt ctatcaggtt ttcaaataaa accaaactac agtga       55

<210> SEQ ID NO 6
<211> LENGTH: 14
<212> TYPE: DNA
<213> ORGANISM: Artificial Sequence
<220> FEATURE:
<223> OTHER INFORMATION: wild-type 3' UTR sequence from BCL2 nucleotide
      sequence

<400> SEQUENCE: 6
accugacaaa aaaa                                                     14

<210> SEQ ID NO 7
<211> LENGTH: 14
<212> TYPE: DNA
<213> ORGANISM: Artificial Sequence
<220> FEATURE:
<223> OTHER INFORMATION: mutant 3' UTR sequence from BCL2 nucleotide
      sequence

<400> SEQUENCE: 7
accugauaag acaa                                                     14
```